(12) United States Patent
Kudo et al.

(10) Patent No.: US 12,217,387 B2
(45) Date of Patent: Feb. 4, 2025

(54) LEARNING METHOD, LEARNING SYSTEM, LEARNED MODEL, PROGRAM, AND SUPER RESOLUTION IMAGE GENERATING DEVICE

(71) Applicant: FUJIFILM Corporation, Tokyo (JP)

(72) Inventors: Akira Kudo, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 709 days.

(21) Appl. No.: 17/400,142

(22) Filed: Aug. 12, 2021

(65) Prior Publication Data

US 2021/0374911 A1 Dec. 2, 2021

Related U.S. Application Data

(63) Continuation of application No. PCT/JP2020/007383, filed on Feb. 25, 2020.

(30) Foreign Application Priority Data

Feb. 28, 2019 (JP) ................................. 2019-036374

(51) Int. Cl.
*G06T 3/4053* (2024.01)
*G06N 3/045* (2023.01)
(Continued)

(52) U.S. Cl.
CPC .......... *G06T 3/4053* (2013.01); *G06N 3/045* (2023.01); *G06N 3/088* (2013.01); *G06T 3/40* (2013.01);
(Continued)

(58) Field of Classification Search
CPC ....... G06T 3/4053; G06T 3/40; G06T 3/4046; G06T 5/002; G06T 5/20; G06T 2200/04;
(Continued)

(56) References Cited

U.S. PATENT DOCUMENTS

2018/0075581 A1 3/2018 Shi et al.
2018/0341836 A1 11/2018 Lim et al.
(Continued)

FOREIGN PATENT DOCUMENTS

EP 3447721 2/2019

OTHER PUBLICATIONS

"Office Action of Japan Counterpart Application" with English translation thereof, issued on Apr. 26, 2022, p. 1-p. 4.
(Continued)

*Primary Examiner* — Charles T Shedrick
(74) *Attorney, Agent, or Firm* — JCIPRNET

(57) ABSTRACT

Provided are a learning method and a learning system of a generative model, a program, a learned model, and a super resolution image generating device that can handle input data of any size and can suppress the amount of calculation at the time of image generation. A learning method according to an embodiment of the present disclosure is a learning method for performing machine learning of a generative model that estimates, from a first image, a second image including higher resolution image information than the first image, the method comprising using a generative adversarial network including a generator which is the generative model and a discriminator which is an identification model that identifies whether provided data is data of a correct image for learning or data derived from an output from the generator and implementing a self-attention mechanism only in a network of the discriminator among the generator and the discriminator.

19 Claims, 21 Drawing Sheets

(51) Int. Cl.
  *G06N 3/088* (2023.01)
  *G06T 3/40* (2024.01)
  *G06T 3/4046* (2024.01)
  *G06T 5/20* (2006.01)
  *G06T 5/70* (2024.01)

(52) U.S. Cl.
  CPC ............ *G06T 3/4046* (2013.01); *G06T 5/20* (2013.01); *G06T 5/70* (2024.01); *G06T 2200/04* (2013.01); *G06T 2207/10081* (2013.01); *G06T 2207/20081* (2013.01); *G06T 2207/20084* (2013.01)

(58) Field of Classification Search
  CPC . G06T 2207/10081; G06T 2207/20081; G06T 2207/20084; G06T 2207/30004; G06N 3/045; G06N 3/088; G06N 3/047; A61B 5/00; A61B 6/03
  See application file for complete search history.

(56) References Cited

U.S. PATENT DOCUMENTS

2019/0057488 A1    2/2019  Li
2021/0237767 A1*   8/2021  Khoreva ................ G06N 3/045
2021/0374911 A1*  12/2021  Kudo .................... G06N 3/047

OTHER PUBLICATIONS

"Search Report of Europe Counterpart Application", issued on Mar. 23, 2022, pp. 1-8.
Christian Ledig et al., "Photo-Realistic Single Image Super-Resolution Using a Generative Adversarial Network", 2017 IEEE Conference on Computer Vision and Pattern Recognition (CVPR), Jul. 2017, pp. 1-14.
Junyoung Park et al., "Computed tomography super-resolution using deep convolutional neural network", Physics in Medicine & Biology, vol. 63, Issue 14, Jul. 2018, pp. 1-13.
Zhengchun Liu et al., "TomoGAN: low-dose synchrotron x-ray tomography with generative adversarial networks: discussion", Journal of the Optical Society of America A, vol. 37, Issue 3, Mar. 2020, pp. 1-17.
Khizar Hayat, "Multimedia super-resolution via deep learning: A survey", Digital Signal Processing, vol. Oct. 2018, pp. 198-217.
Ian J. Goodfellow et al., "Generative Adversarial Nets," arXiv:1406.2661, Jun. 2014, pp. 1-9.
Phillip Isola et al., "Image-to-Image Translation with Conditional Adversarial Networks," CVPR2016, Nov. 2016, pp. 1-17.
Han Zhang et al., "Self-Attention Generative Adversarial Networks," arXiv:1805.08318, May 2018, pp. 1-10.
Harsh Nilesh Pathak et al., "Efficient Super Resolution For Large-Scale Images Using Attentional GAN," IEEE International Conference on Big Data, Dec. 2018, pp. 1777-1786.
"International Search Report (Form PCT/ISA/210) of PCT/JP2020/007383," mailed on Apr. 14, 2020, with English translation thereof, pp. 1-5.
"Written Opinion of the International Searching Authority (Form PCT/ISA/237)" of PCT/JP2020/007383, mailed on Apr. 14, 2020, with English translation thereof, pp. 1-7.

* cited by examiner

| SLICE INTERVAL | STANDARD DEVIATION σ (GAUSSIAN FILTER) | ASSUMED SLICE THICKNESS |
|---|---|---|
| 4 mm | 0 TO 1.6 | ORIGINAL SLICE THICKNESS + 0 TO 4 mm |
| 8 mm | 0 TO 3.2 | ORIGINAL SLICE THICKNESS + 0 TO 8 mm |

LEARNING METHOD, LEARNING SYSTEM, LEARNED MODEL, PROGRAM, AND SUPER RESOLUTION IMAGE GENERATING DEVICE

CROSS-REFERENCE TO RELATED APPLICATIONS

The present application is a Continuation of PCT International Application No. PCT/JP2020/007383 filed on Feb. 25, 2020 claiming priority under 35 U.S.C. § 119(a) to Japanese Patent Application No. 2019-036374 filed on Feb. 28, 2019. Each of the above applications is hereby expressly incorporated by reference, in its entirety, into the present application.

BACKGROUND OF THE INVENTION

1. Field of the Invention

The present invention relates to a learning method, a learning system, a learned model, a program, and a super resolution image generating device, and more particularly to a machine learning technique and an image processing technique for realizing super resolution image generation.

2. Description of the Related Art

In recent years, a technique for generating an image by performing machine learning by using a multi-layer neural network has been proposed. US2018/0075581A discloses a method for learning a generative model by using a generative adversarial network (GAN) to realize super resolution image generation. Ian J. Goodfellow, Jean Pouget-Abadie, Mehdi Mirza, Bing Xu, David Warde-Farley, Sherjil Ozair, Aaron Courville, Yoshua Bengio "Generative Adversarial Nets", arXiv: 1406.2661 discloses a study of the GAN. The GAN includes a generation network called a generator which produces data and an identification network called a discriminator which identifies the data. The discriminator identifies whether the input data is the correct data from the learning data or the data derived from the output of the generator. It is a goal that by alternately updating the generator and the discriminator in a case of learning and increasing the accuracy of both the generator and the discriminator, the generator can generate the data close to the learning data.

Phillip Isola, Jun-Yon Zhu, Tinghui Zhou, Alexei A. Efros "Image-to-Image Translation with Conditional Adversarial Networks", CVPR2016 discloses a method for learning a pair of an input image and an output image by using the GAN. Han Zhang, Ian Goodfellow, Dimitris Metaxas, Augustus Odena "Self-Attention Generative Adversarial Networks", arXiv: 1805.08318 discloses a study in which a self-attention mechanism is introduced into the GAN. The self-attention mechanism is a mechanism for adding wide area information to the feature map output from the hidden layer of the network. In the method disclosed in Han Zhang, Ian Goodfellow, Dimitris Metaxas, Augustus Odena "Self-Attention Generative Adversarial Networks", arXiv: 1805.08318, the self-attention mechanism is introduced in both the networks of the generator and the discriminator, and a high resolution image can be generated for input data of a specific size.

SUMMARY OF THE INVENTION

However, the method disclosed in Han Zhang, Ian Goodfellow, Dimitris Metaxas, Augustus Odena "Self-Attention Generative Adversarial Networks", arXiv: 1805.08318 has the following problems.

[Problem 1] In the method disclosed in Han Zhang, Ian Goodfellow, Dimitris Metaxas, Augustus Odena "Self-Attention Generative Adversarial Networks", arXiv: 1805.08318, since the generator has the attention mechanism, it is necessary that the data to be input to the generator at the time of learning and at the time of estimation after learning have the same input size. That is, the size of the data that can be input to the learned generator is restricted to a fixed size, and any input size cannot be handled.

[Problem 2] In the method disclosed in Han Zhang, Ian Goodfellow, Dimitris Metaxas, Augustus Odena "Self-Attention Generative Adversarial Networks", arXiv: 1805.08318, since the generator has the attention mechanism, the amount of calculation of the generator is increased at the time of image generation (at the time of estimation). In particular, the amount of calculation is increased exponentially in a case in which the input image size is increased.

The present invention has been made in view of such circumstances, and is to provide a learning method and a learning system of a generative model, a program, a learned model, and a super resolution image generating device that can handle input data of any size without being restricted by the image size at the time of learning and can suppress the amount of calculation at the time of image generation.

A learning method according to an aspect of the present disclosure is a learning method for performing machine learning of a generative model that estimates, from a first image, a second image including higher resolution image information than the first image, the method comprising using a generative adversarial network including a generator which is the generative model and a discriminator which is an identification model that identifies whether provided data is data of a correct image for learning or data derived from an output from the generator, using, as learning data, a first learning image including first resolution information having a lower resolution than the second image and a second learning image including second resolution information having a higher resolution than the first learning image, the second learning image being the correct image corresponding to the first learning image, providing only the first learning image, among the first learning image and the second learning image, to be input to the generator, and implementing a self-attention mechanism only in a network of the discriminator among the generator and the discriminator.

According to the aspect, by introducing the self-attention mechanism, the wide information of the image is taken into consideration in the learning, and the learning is performed with high accuracy. According to the aspect, it is possible to improve the accuracy of the generated image without increasing the amount of calculation of the generator by introducing the self-attention mechanism only for the discriminator. Further, since the generator does not comprise the self-attention mechanism, it is possible to generate an image with high accuracy for input data of any size.

In the learning method according to another aspect of the present disclosure, each network of the generator and the discriminator may be a convolutional neural network.

In the learning method according to still another aspect of the present disclosure, the first image may be a three-dimensional tomographic image, and the second image may have at least a higher resolution than the first image in a slice thickness direction of the three-dimensional tomographic image.

In the learning method according to still another aspect of the present disclosure, the second learning image may be an image acquired by using a computed tomography device, and the first learning image may be an image generated by image processing based on the second learning image.

In the learning method according to still another aspect of the present disclosure, the image processing of generating the first learning image from the second learning image may include down-sampling processing of the second learning image.

In the learning method according to still another aspect of the present disclosure, the image processing of generating the first learning image from the second learning image may include up-sampling processing of an image obtained by the down-sampling processing by performing interpolation processing.

In the learning method according to still another aspect of the present disclosure, the image processing of generating the first learning image from the second learning image may include smoothing processing using a Gaussian filter.

In the learning method according to still another aspect of the present disclosure, the first learning images and the second learning images in a plurality of types of the learning data used for the machine learning may have the same size, respectively.

In the learning method according to still another aspect of the present disclosure, the second image may be a high-frequency component image indicating information of a high-frequency component, and the generator may estimate a high-frequency component required to increase a resolution of an input image and output the high-frequency component image indicating the information of the high-frequency component.

The learning method according still another aspect of the present disclosure may further comprise adding the high-frequency component image output from the generator and the image input to the generator, in which a virtual second image obtained by the adding is provided to be input to the discriminator.

A program according to still another aspect of the present disclosure is a program that causes a computer to execute the learning method according to any one of the aspects of the present disclosure.

A learned model according to still another aspect of the present disclosure is a learned model that is learned by performing the learning method according to any one of the aspects of the present disclosure, the learned model being the generative model that estimates, from the first image, the second image including higher resolution image information than the first image.

A super resolution image generating device according to still another aspect of the present disclosure is a super resolution image generating device comprising the generative model which is a learned model that is learned by performing the learning method according to any one of the aspects of the present disclosure, in which the super resolution image generating device generates, from a third image which is input, a fourth image including higher resolution image information than the third image.

With the super resolution image generating device according to the aspect, it is possible to generate an image with high accuracy for input data of any size.

In the super resolution image generating device according to still another aspect of the present disclosure, an image size of the third image may be different from an image size of the first learning image.

The super resolution image generating device according to still another aspect of the present disclosure may further comprise a first interpolation processing unit that performs interpolation processing on the third image to generate an interpolation image, and a first addition unit that adds the interpolation image and a high-frequency component generated by the generative model, in which the interpolation image is input to the generative model, and the generative model generates the high-frequency component required to increase a resolution of the interpolation image.

A learning system according to still another aspect of the present disclosure is a learning system for performing machine learning of a generative model that estimates, from a first image, a second image including higher resolution image information than the first image, the system comprising a generative adversarial network including a generator which is the generative model and a discriminator which is an identification model that identifies whether provided data is data of a correct image for learning or data derived from an output from the generator, in which a self-attention mechanism is implemented only in a network of the discriminator among the generator and the discriminator, a first learning image including first resolution information having a lower resolution than the second image and a second learning image including second resolution information having a higher resolution than the first learning image, the second learning image being the correct image corresponding to the first learning image are used as learning data, and only the first learning image among the first learning image and the second learning image is provided to be input to the generator and learning of the generative adversarial network is performed.

In the learning system according to still another aspect of the present disclosure may further comprise a learning data generating unit that generates the learning data, in which the learning data generating unit includes a fixed-size region cutout unit that cuts out a fixed-size region from an original image including the second resolution information, and a down-sampling processing unit that performs down-sampling of an image of the fixed-size region cut out by the fixed-size region cutout unit, the image of the fixed-size region cut out by the fixed-size region cutout unit is used as the second learning image, and the first learning image is generated by performing down-sampling processing on the second learning image.

In the learning system according to still another aspect of the present disclosure, the learning data generating unit may further include a second interpolation processing unit that performs interpolation processing on an image obtained by the down-sampling processing, and a smoothing processing unit that performs smoothing by using a Gaussian filter.

In the learning system according to still another aspect of the present disclosure, the generator may be configured to estimate a high-frequency component required to increase a resolution of an input image and output the high-frequency component image indicating the information of the high-frequency component, and the learning system may further comprise a second addition unit that adds the high-frequency component image output from the generator and the image input to the generator.

A learning system according to still another aspect of the present disclosure is a learning system for performing machine learning of a generative model that estimates, from a first image, a second image including higher resolution image information than the first image, the system comprising at least one processor, in which the processor includes a generative adversarial network including a generator which is the generative model and a discriminator which is an identification model that identifies whether provided data is data of a correct image for learning or data derived from an output from the generator, in which a self-attention mechanism is implemented only in a network of the discriminator among the generator and the discriminator, a first learning image including first resolution information having a lower resolution than the second image and a second learning image including second resolution information having a higher resolution than the first learning image, the second learning image being the correct image corresponding to the first learning image are used as learning data, and only the first learning image among the first learning image and the second learning image is provided to be input to the generator and learning of the generative adversarial network is performed.

According to the present invention, it is possible to obtain a generative model capable of generating a high resolution image for input data of any size. Further, according to the present invention, it is possible to obtain a generative model capable of suppressing the amount of calculation at the time of image generation, and it is possible to realize high accuracy image generation using the learned model.

DESCRIPTION OF THE PREFERRED EMBODIMENTS

Preferred embodiments of the present invention will be described below in detail with reference to the accompanying drawings.

First Embodiment

A super resolution image generating device according to an embodiment of the present invention generates virtual high resolution image data from low resolution image data. "Generate" includes the concept of the term "estimate". Here, as a specific example of the image data, data of a computed tomography (CT) image acquired by using a CT device is targeted, and a super resolution image generating device is described as an example, which generates virtual thin slice image data from thick slice image data acquired by using the CT device.

The thick slice image data refers to low resolution CT image data having a relatively large slice interval and slice thickness. For example, the CT image data having a slice interval and a slice thickness of more than 4 mm corresponds to the thick slice image data. The thick slice image data may be referred to as "thick slice image", "thick slice data", or "thick data".

The thin slice image data is high resolution CT image data having a small slice interval and slice thickness. For example, the CT image data having the slice interval and the slice thickness of about 1 mm corresponds to the thin slice image data. The thin slice image data may be referred to as "thin slice image", "thin slice data", or "thin data".

In the present embodiment, the virtual thin slice image generated from the thick slice image is referred to as a virtual thin slice (VTS) image. On the other hand, a real thin slice image acquired by imaging with the CT device is referred to as a real thin slice (RTS) image.

Explanation of CT Image Data

Figure 1:
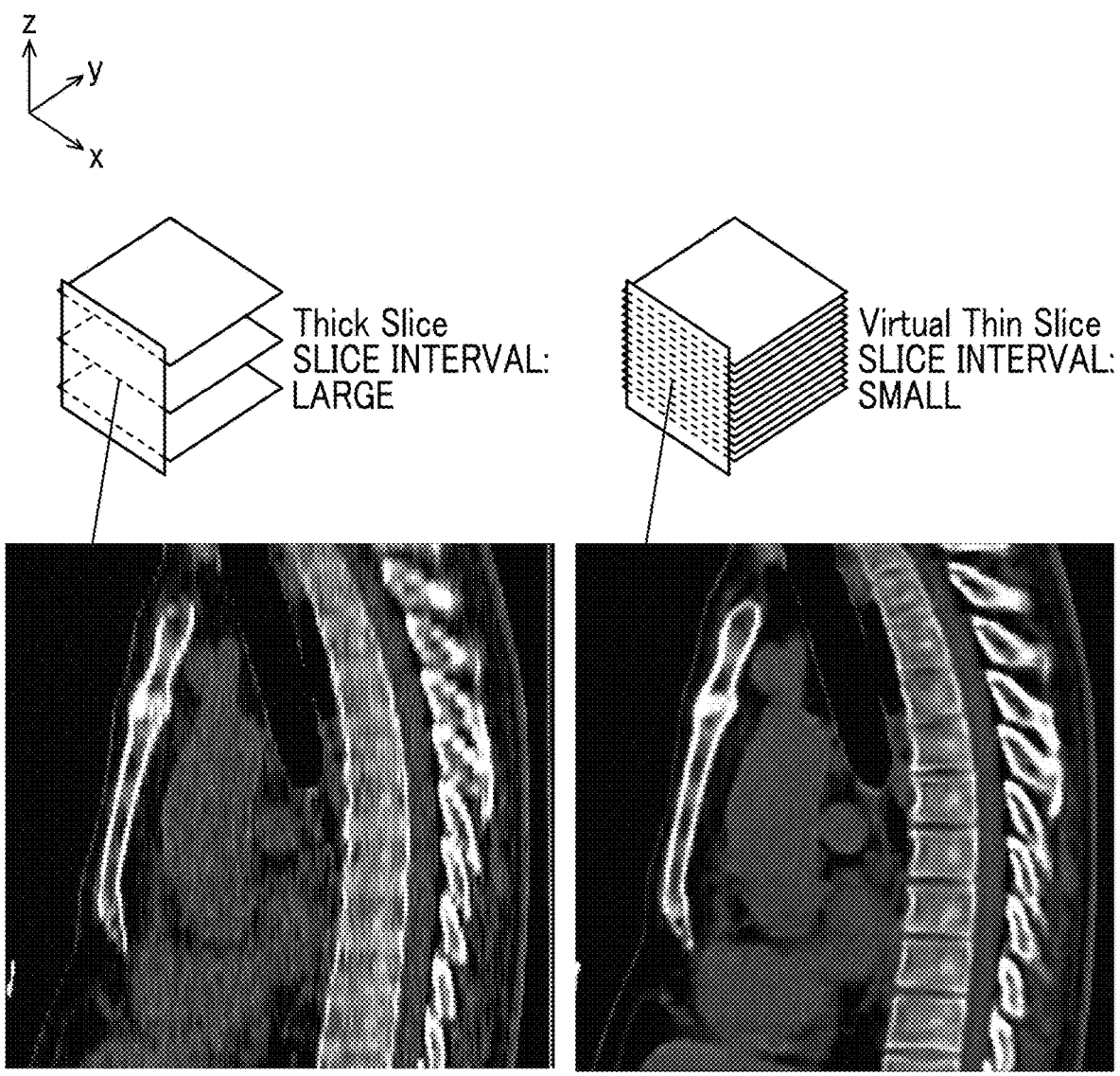
FIG. 1 is an image diagram of data of each of a thick slice image and a virtual thin slice image.

FIG. 1 is an image diagram of each data of the thick slice image and the VTS image. The left side of FIG. 1 is the thick slice image, and the right side of FIG. 1 is the VTS image. The VTS image can generate a reconstructed image having a high quality as compared with the thick slice image. In FIG. 1, the Z-axis direction is the body axis direction.

As the CT data, data having various slice intervals and slice thicknesses may be present depending on the model of the CT device used for imaging and depending on the setting of output slice conditions and the like.

FIGS. 2 to 5 are diagrams for explaining examples of the slice interval and the slice thickness of the CT image. The slice interval is the distance between the center positions of the thicknesses of a slice and the adjacent slice. The slice interval is synonymous with the distance between the slices. The slice thickness refers to the length in the thickness direction of one slice at the center position of an imaging region. The slice thickness is synonymous with a slice thickness. In FIGS. 2 to 5, the slice interval is displayed as SD and the slice thickness is displayed as ST. The thickness direction of the slice is the Z-axis direction.

Figure 2:
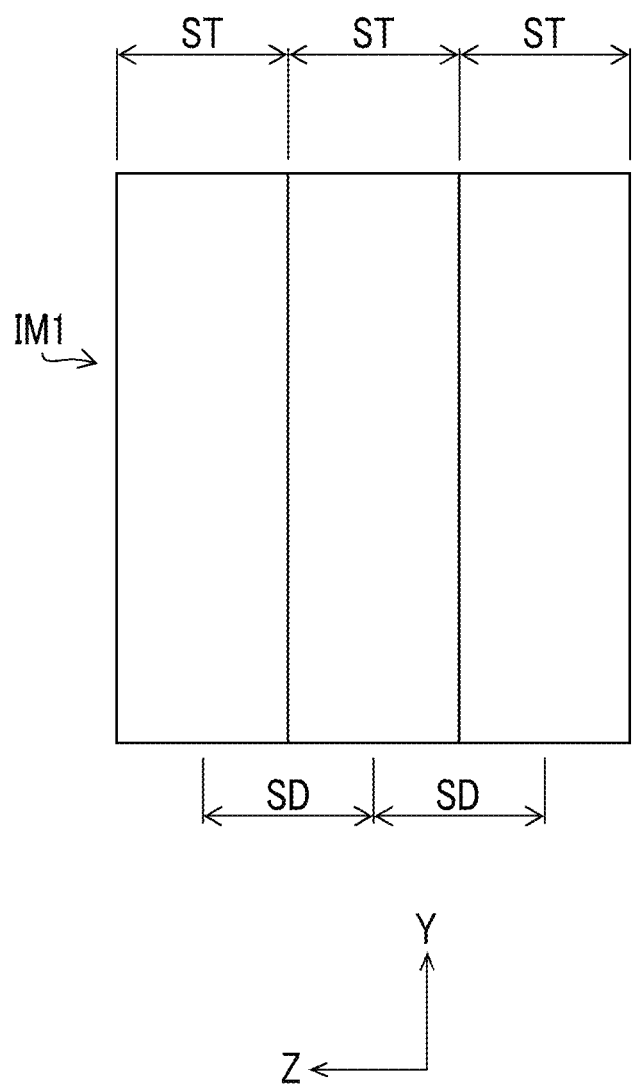
FIG. 2 is a diagram for explaining a slice interval and a slice thickness of a CT image.

FIG. 2 is an explanatory diagram schematically showing a CT image IM1 in a case in which a slice interval SD is 4 mm and a slice thickness ST is 4 mm. Here, for the sake of simplicity, a three-layer tomographic image group is shown schematically.

Figure 3:
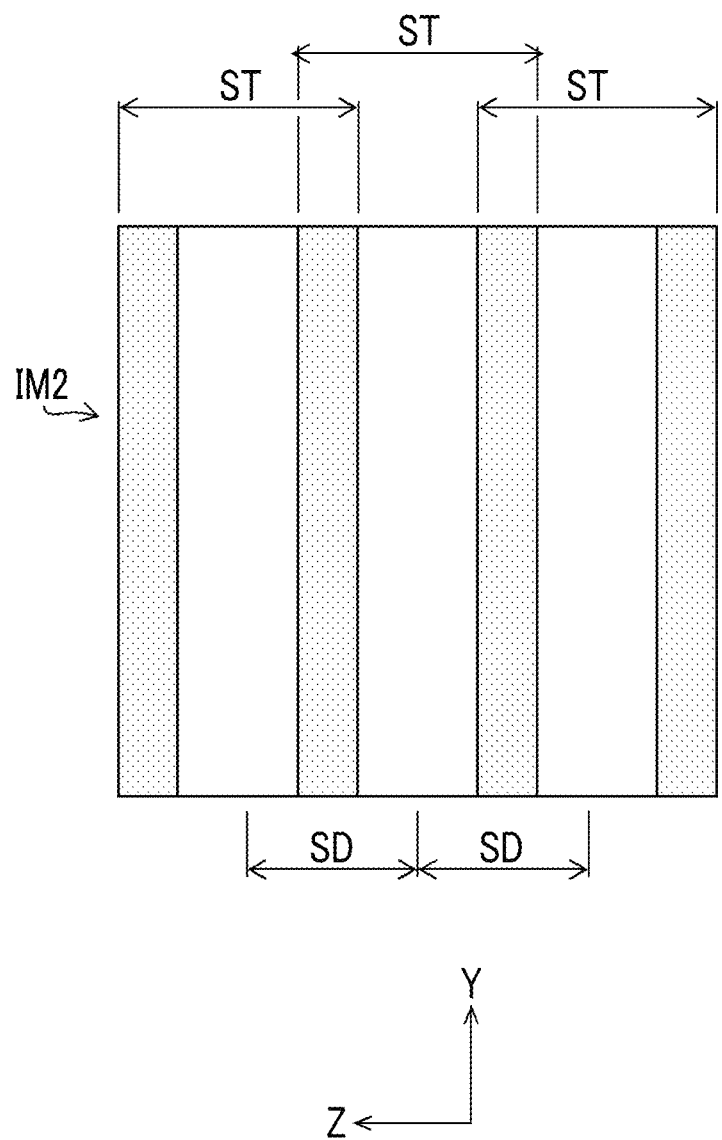
FIG. 3 is a diagram for explaining the slice interval and the slice thickness of the CT image.

FIG. 3 is an explanatory diagram schematically showing a CT image IM2 in a case in which the slice interval SD is 4 mm and the slice thickness ST is 6 mm. In the case of FIG. 3, the slice thickness ranges overlap between the adjacent slices.

Figure 4:
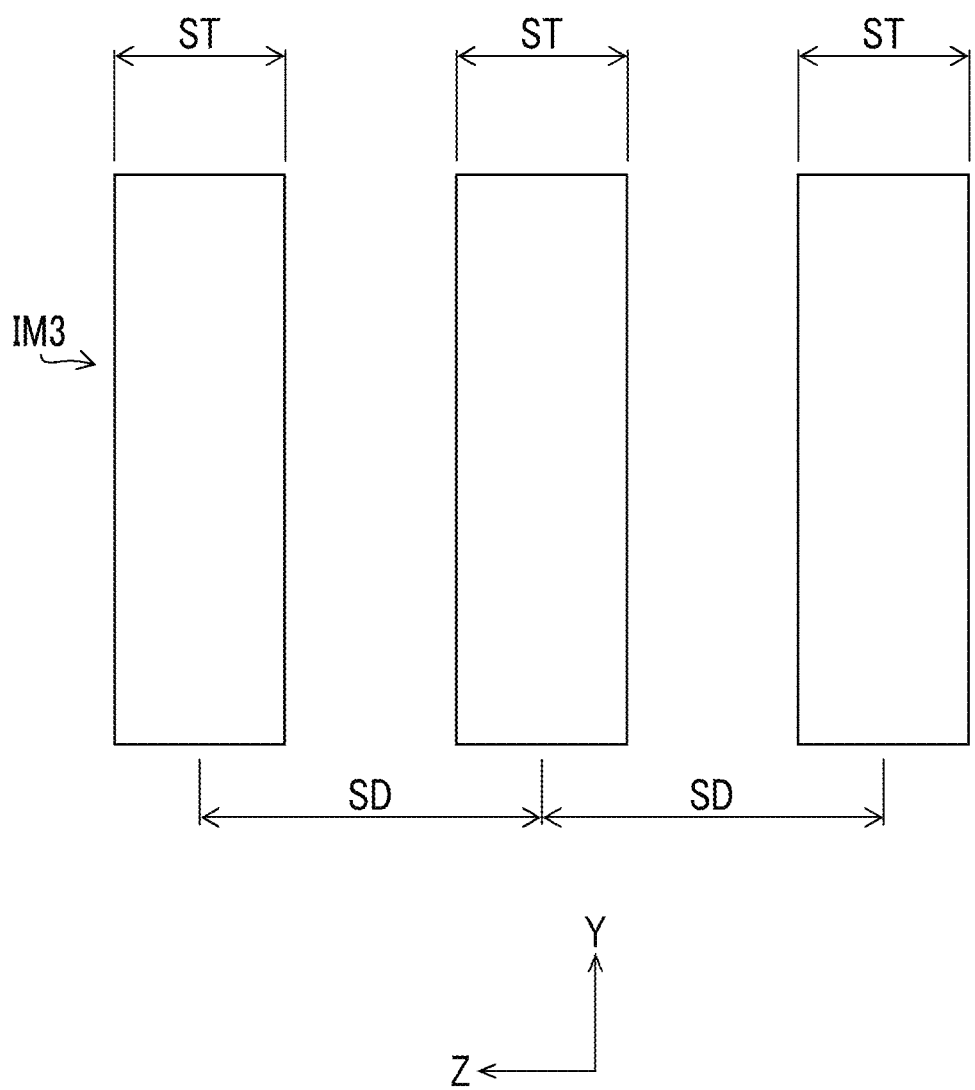
FIG. 4 is a diagram for explaining the slice interval and the slice thickness of the CT image.

FIG. 4 is an explanatory diagram schematically showing a CT image IM3 in a case in which the slice interval SD is 8 mm and the slice thickness ST is 4 mm. In the case of the example of FIG. 4, the slice interval SD is larger than the slice thickness ST, and thus adjacent tomographic images are separated from each other and there is a gap between the layers.

Figure 5:
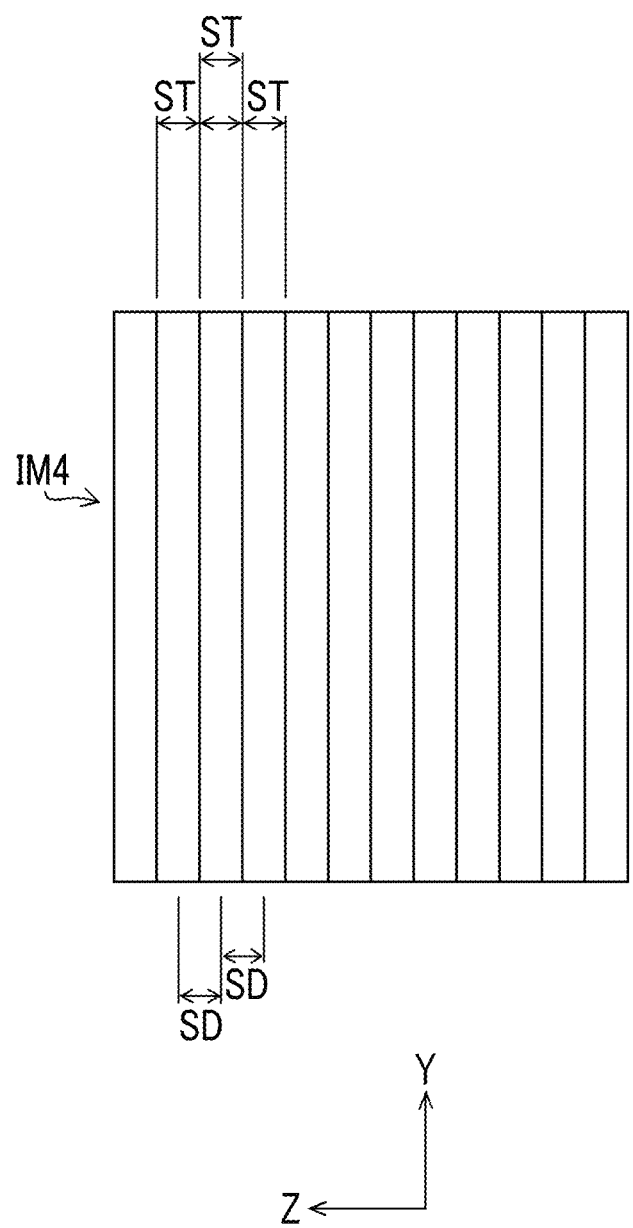
FIG. 5 is a diagram for explaining the slice interval and the slice thickness of the CT image.

FIG. 5 is an explanatory diagram schematically showing a CT image IM4 in which the slice interval SD is 1 mm and the slice thickness ST is 1 mm. The CT image Im4 shown in FIG. 5 has a larger amount of information in the Z direction than the other CT images IM1 to IM3 shown in FIGS. 2 to 4. That is, the CT image IM4 has a relatively higher resolution than any of the CT images IM1, IM2, and IM3 in the Z direction.

The slice interval and slice thickness of the CT image are set under various conditions depending on the facility at which the CT device is used, the preference of a doctor, and the like. It is preferable that the CT image have a high resolution for diagnosis, but there is a problem that in a case in which the slice interval is reduced, the amount of exposure to a subject is increased. In addition, the high resolution CT image has a large amount of data and presses a storage capacity of a storage, so that the CT image may be stored at a lower resolution in order to reduce the capacity. For example, the old CT data is stored in a database by reducing the number of imaged slices.

However, the thick slice image has a problem that it is difficult to use for sufficient observation and analysis because the quality of the reconstructed image or a volume rendered image viewed from a side surface with a surface parallel to the body axis as a cross section is poor.

The super resolution image generating device according to the present embodiment performs image generation processing of generating the high resolution VTS image having, for example, the slice interval of 1 mm and the slice thickness of 1 mm as shown in FIG. 5 from the low resolution CT image of various slice conditions (slice interval and slice thickness) as shown in FIGS. 3 to 5.

Figure 6:
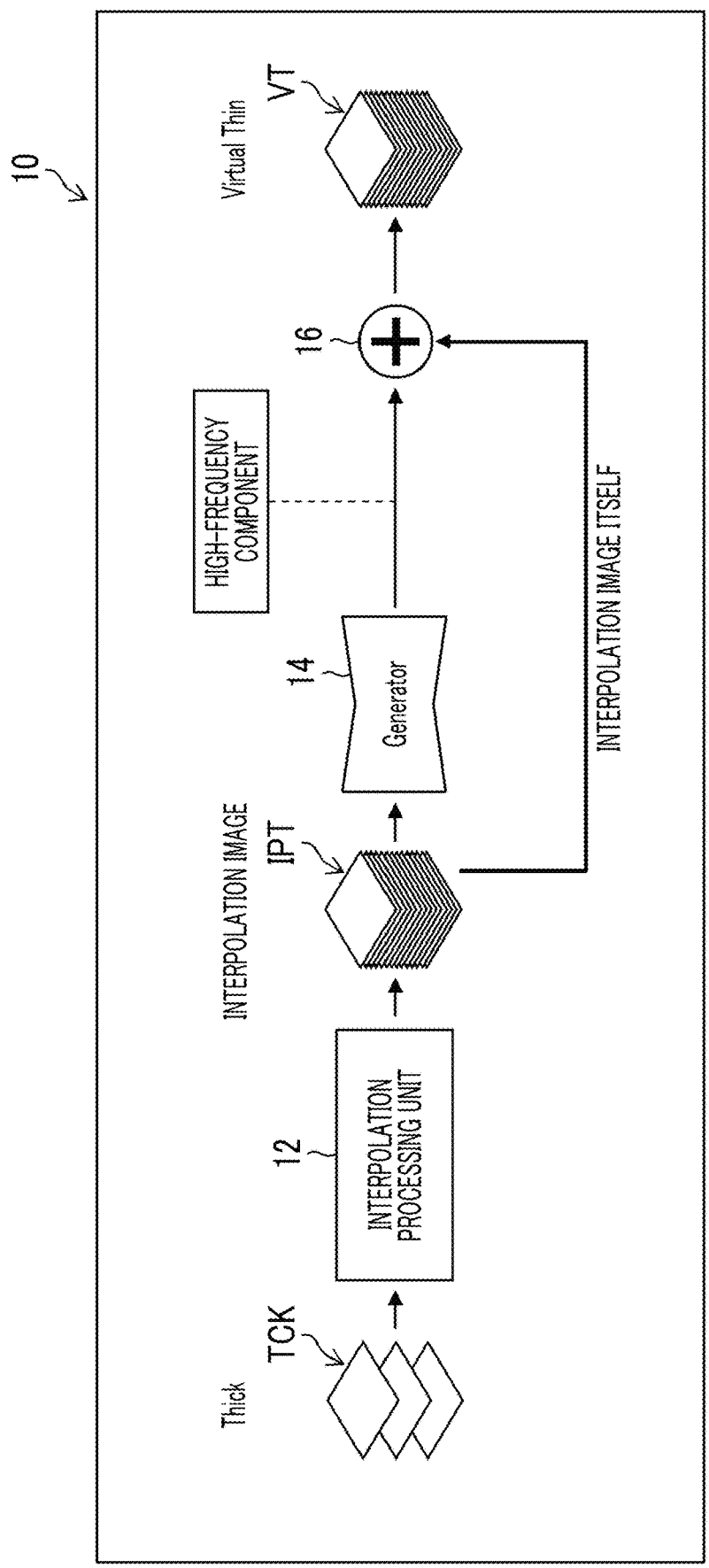
FIG. 6 is a functional block diagram showing an example of a super resolution image generating device according to an embodiment of the present invention.

Example of Image Generation Algorithm in Super Resolution Image Generating Device FIG. 6 is a functional block diagram showing an example of the super resolution image generating device according to the embodiment of the present invention. The super resolution image generating device 10 includes an interpolation processing unit 12, a generator 14 which is a learned model of a multilayered neural network, and an addition unit 16. The "neural network" is a mathematical model of information processing that simulates a mechanism of a cranial nerve system. Processing using the neural network can be realized by using a computer. The neural network can be configured as a program module. In the present specification, the neural network may be simply referred to as a "network".

The interpolation processing unit 12 performs spline interpolation on an input low resolution thick slice image TCK to generate an interpolation image IPT. The interpolation image IPT output from the interpolation processing unit 12 is an image blurred in the Z direction, and is an example of a low resolution image. It is preferable that the number of pixels of the interpolation image IPT match the number of pixels of a finally generated virtual thin slice image VT.

The interpolation image IPT output from the interpolation processing unit 12 is input to the generator 14. The generator 14 is a generative model learned by machine learning by using a generative adversarial network (GAN). A learning method for obtaining the generator 14 will be described below. The learned model may be also referred to as the program module.

The generator 14 generates (estimates) high-frequency component information required to generate a high resolution image from the input image, and outputs the high-frequency component information.

The addition unit 16 adds a map of the high-frequency component information output from the generator 14 and the interpolation image IPT itself which is the input data of the generator 14 to generate the virtual thin slice image VT.

FIG. 6 shows an example in which the input to the generator 14 is the interpolation image IPT and the output of the generator 14 is the high-frequency component information, but a form in which the input to the generator 14 is the thick slice image TCK can also be adopted. A form in which the output of the generator 14 is the virtual thin slice image VT can also be adopted. Since the high-frequency component information is information that can generate the high resolution image by adding the original image, the map of the high-frequency component information is called the "high-frequency component image". The high-frequency component image is an image including high resolution image information, and can be understood as substantially the same as the "high resolution image".

In FIG. 6, the thick slice image TCK is an example of a "third image" in the present disclosure. The virtual thin slice image VT is an example of a "fourth image" in the present disclosure. The high-frequency component output from the generator 14 is an example of "higher resolution image information than the third image" in the present disclosure. The interpolation processing unit 12 is an example of a "first interpolation processing unit" in the present disclosure. The addition unit 16 is an example of a "first addition unit" in the present disclosure.

Configuration Example of Learning System

Next, the learning method for generating the generator 14 will be described.

Figure 7:
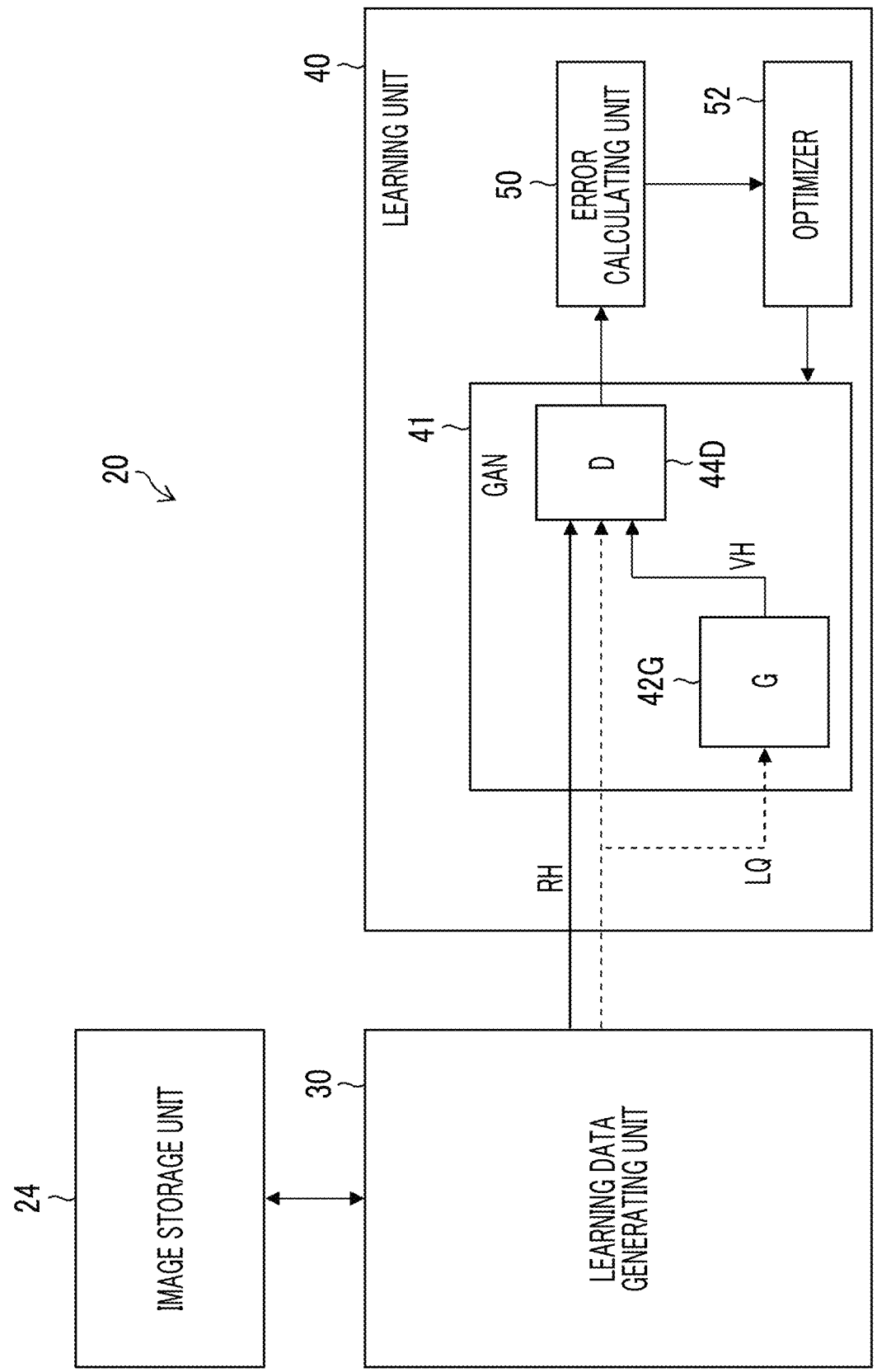
FIG. 7 is a block diagram showing a configuration example of a learning system according to the embodiment of the present invention.

FIG. 7 is a block diagram showing a configuration example of a learning system 20 according to the embodiment of the present invention. The learning system 20 includes an image storage unit 24, a learning data generating unit 30, and a learning unit 40. The learning system 20 can be realized by a computer system including one or a plurality of the computers. That is, the functions of the image storage unit 24, the learning data generating unit 30, and the learning unit 40 can be realized by a combination of a hardware and a software of the computer. Here, an example in which the image storage unit 24, the learning data generating unit 30, and the learning unit 40 are configured as separate devices will be described, but these functions may be realized by one computer, or the processing functions may be allocated and realized by two or more computers. For example, the image storage unit 24, the learning data generating unit 30, and the learning unit 40 may be connected to each other via a communication line. The term "connection" is not limited to wired connection, and also includes the concept of wireless connection. The communication line may be a local area network, or may be a wide area network.

With this configuration, the generation of the learning data and the learning of the generative model can be performed without being physically and temporally restricted by each other.

The image storage unit 24 includes a large-capacity storage device that stores a CT reconstructed image (CT image) captured by a medical X-ray CT device. The image storage unit 24 may be, for example, a storage in a medical image management system represented by a picture archiving and communication system (PACS). The image storage unit 24 stores data of a plurality of thin slice images, which are real high resolution images captured by using the CT device (not shown).

The CT image stored in the image storage unit 24 is a medical image obtained by imaging a human body (subject), and is a three-dimensional tomographic image including a plurality of tomographic images. Here, each tomographic image is an image parallel to the X direction and the Y direction which are orthogonal to each other. The Z direction orthogonal to the X direction and the Y direction is the body axis direction of the subject, and is also referred to as a slice thickness direction. The CT image stored in the image storage unit 24 may be an image for each part of the human body or an image obtained by imaging the whole body.

The learning data generating unit 30 generates the learning data required for the learning unit 40 to perform learning. The learning data is data for training used for machine learning, and is synonymous with "data for learning" or "training data". In the machine learning of the present embodiment, a large number of learning data of an image pair in which a low resolution image for input and a high resolution correct image corresponding to the low resolution image are associated are used. Such an image pair can be artificially generated by image processing based on the thin slice data which is the real high resolution image.

The learning data generating unit 30 acquires an original real high resolution image from the image storage unit 24 and performs down-sampling processing on the real high resolution image to artificially generate various low resolution images (pseudo thick slice images). The learning data generating unit 30 performs posture conversion on, for example, the original thin slice data equalized to 1 mm, randomly cuts out a fixed-size region, and then generates virtual 4 mm slice data having the slice interval of 4 mm and virtual 8 mm slice data having the slice interval of 8 mm. The fixed-size region may be a three-dimensional region in which the number of pixels in X-axis direction×Y-axis direction×Z-axis direction is, for example, "160×160×160". The learning data generating unit 30 generates an image pair of a fixed-size low resolution image LQ for learning and a real high resolution image RH corresponding to the fixed-size low resolution image LQ.

In order to perform the learning processing by the learning unit 40, it is preferable that a plurality of pieces of the learning data be generated in advance from the original real high resolution image by using the learning data generating unit 30, and stored in the storage as a learning data set.

The low resolution image LQ and the real high resolution image RH which are generated by the learning data generating unit 30 are input to the learning unit 40.

The learning unit 40 includes a generative adversarial network (GAN) 41 as a learning model. The architecture of the learning unit 40 is based on a structure obtained by extending the architecture disclosed in Phillip Isola, Jun-Yan Zhu, Tinghui Zhou, Alexei A. Efros "Image-to-Image Translation with Conditional Adversarial Networks", CVPR2016 from two-dimensional data to three-dimensional data. The GAN 41 is configured to include the generation network called a generator 42G that produces the data and the identification network called a discriminator 44D that identifies the input data. That is, the generator 42G is a generative model that generates the image data, and the discriminator 44D is an identification model that identifies the data. The term "generator" is synonymous with terms such as "generating unit", "generating device", and "generative model". The term "discriminator" is synonymous with terms such as "identification unit", "identification device", and "identification model".

By repeating adversarial learning by using the generator 42G and the discriminator 44 based on the input learning data, the learning unit 40 learns the generator 42G while improving the performance of both models.

A self-attention mechanism is implemented in the discriminator 44D in this example. The layer to which the self-attention mechanism is introduced in the network of the discriminator 44D may be a part or all of a plurality of convolutional layers. Details of the configuration and the operation of the discriminator 44D including the self-attention mechanism and an example of the learning method of the GAN 41 will be described below.

The learning unit 40 includes an error calculating unit 50 and an optimizer 52. The error calculating unit 50 evaluates an error between the output of the discriminator 44D and the correct answer using the loss function. The optimizer 52 performs processing of updating network parameters based on the calculation result of the error calculating unit 50. The network parameters include a filter coefficient (weight of connection between nodes) of filters used to process each layer, node bias, and the like.

The optimizer 52 performs parameter calculation processing of calculating the update amount of the parameters of each network of the generator 42G and the discriminator 44D from the calculation result of the error calculating unit 50, and parameter update processing of updating the parameters of each network of the generator 42G and the discriminator 44D depending on the calculation result of the parameter calculation processing. The optimizer 52 updates the parameters based on the algorithm such as the gradient descent method.

About Generation of Learning Data

Figure 8:
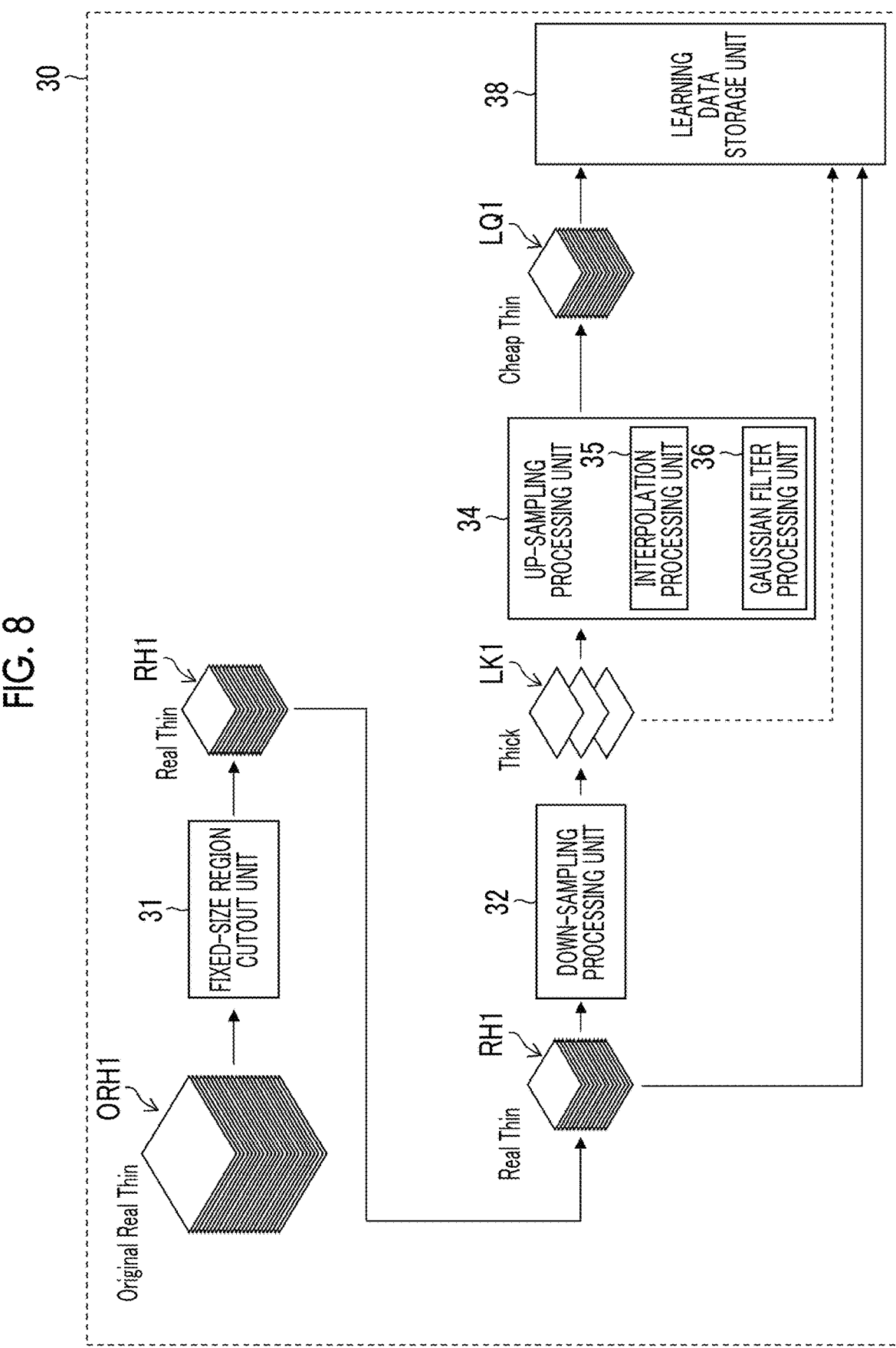
FIG. 8 is a functional block diagram showing a configuration example of a learning data generating unit.

FIG. 8 is a functional block diagram showing a configuration example of the learning data generating unit 30. The learning data generating unit 30 includes a fixed-size region cutout unit 31, a down-sampling processing unit 32, an up-sampling processing unit 34, and a learning data storage unit 38.

The fixed-size region cutout unit 31 performs processing of randomly cutting out the fixed-size region from an input original real high resolution image ORH1. A real high resolution image RH1 of the fixed-size region cut out by the fixed-size region cutout unit 31 is sent to the down-sampling processing unit 32.

The down-sampling processing unit 32 performs down-sampling of the real high resolution image RH1 in the Z-axis direction to generate a low resolution thick slice image LK1. As the down-sampling processing, for example, thinning processing need only be performed so as to simply reduce the slices in the Z-axis direction at a certain rate. In this example, only the down-sampling in the Z-axis direction is performed, and the down-sampling is not performed in the X-axis direction and the Y-axis direction, but a form in which the down-sampling is performed in the X-axis direction and the Y-axis direction can be adopted.

The thick slice image LK1 generated by the down-sampling processing unit 32 is input to the up-sampling processing unit 34.

The up-sampling processing unit 34 performs up-sampling of the thick slice image LK1 in the Z-axis direction to generate a low resolution image LQ1 which is a low quality thin slice image. The up-sampling processing may be, for example, a combination of spline interpolation and Gaussian filter processing. The up-sampling processing unit 34 includes an interpolation processing unit 35 and a Gaussian filter processing unit 36. The interpolation processing unit 35 performs spline interpolation on, for example, the thick slice image LK1. The interpolation processing unit 35 may be the same processing unit as the interpolation processing unit 12 described with reference to FIG. 6. The Gaussian filter processing unit 36 applies a Gaussian filter to the image output from the interpolation processing unit 35 and performs smoothing. The interpolation processing unit 35 shown in FIG. 8 is an example of a "second interpolation processing unit" in the present disclosure. The Gaussian filter processing unit 36 is an example of a "smoothing processing unit" in the present disclosure.

It is preferable that the low resolution image LQ1 output from the up-sampling processing unit 34 be data having the same number of pixels as the real high resolution image RH1. Here, the low resolution image LQ1 and the real high resolution image RH1 have the same size. The low resolution image LQ1 is an image having a low quality (that is, low resolution) as compared with the real high resolution image RH1. The pair in which the low resolution image LQ1 generated in this way is associated with the real high resolution image RH1 which is the generation source thereof is generated is stored in the learning data storage unit 38.

The original real high resolution image ORH1 is an example of an "original image" in the present disclosure. The real high resolution image RH1 is an example of a "second learning image" in the present disclosure. The low resolution image LQ1 is an example of a "first learning image" in the present disclosure. The image information of the low resolution image LQ1 is an example of "first resolution information" in the present disclosure. The image information of the real high resolution image RH1 is an example of "second resolution information" in the present disclosure.

The learning data generating unit 30 changes the cutout position of the fixed-size region from one original real high resolution image ORH1, cuts out a plurality of real high resolution images RH, and generates the low resolution images LQ corresponding to the real high resolution images RH to generate a plurality of image pairs.

Further, the learning data generating unit 30 can generate the low resolution images with various slice conditions by changing the combination of the slice interpolation magnification in the up-sampling processing unit 34 and the conditions of the Gaussian filter applied to the up-sampling processing unit 34. The slice interpolation magnification corresponds to the down-sampling condition in the down-sampling processing unit 32.

Figures 9, 10:
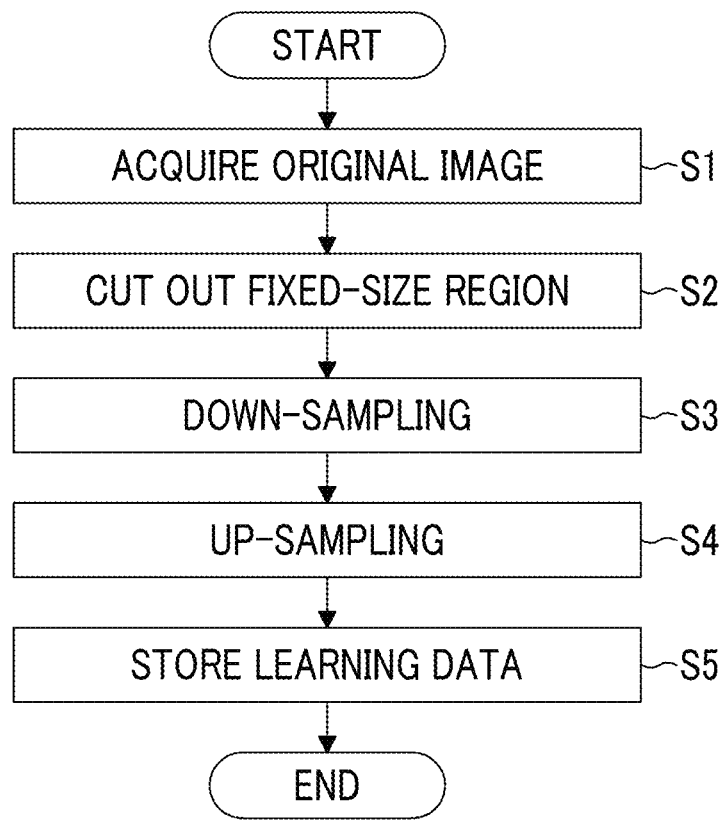
FIG. 9 is a table showing an example of a combination of Gaussian filter conditions corresponding to a slice interval applied in a case in which learning data is generated and an assumed slice thickness.
FIG. 10 is a flowchart showing an example of a procedure for processing of generating the learning data.

It is preferable that the data of various slice conditions be provided in a case of learning. In the present embodiment, learning is performed by using the low resolution images corresponding to various slice conditions as shown in FIG. 9. FIG. 9 is a table showing an example of a combination of the Gaussian filter conditions corresponding to the slice interval applied in a case in which the learning data is generated and an assumed slice thickness.

In this example, the slice intervals of the low resolution image LQ are set to two ways of 4 mm and 8 mm. That is, the slice interpolation magnification at the time of learning has two patterns of 4 times or 8 times. The slice thickness is in a range of 0 mm to 8 mm corresponding to the slice interval. By randomly providing the standard deviation a of the Gaussian filter within the numerical range shown in FIG. 9, the low resolution image in which pseudo various slice thicknesses are assumed can be generated.

By using a plurality of types of the original real high resolution images, a large number of various learning data can be prepared.

Example of Procedure for Processing of Generating Learning Data

FIG. 10 is a flowchart showing an example of a procedure for processing of generating the learning data. Each step of the flowchart shown in FIG. 10 is executed by a computer including a processor that functions as the learning data generating unit 30. The computer comprises a central processing unit (CPU) and a memory. The computer may include a graphics processing unit (GPU).

As shown in FIG. 10, a generation method of the learning data includes an original image acquiring step (step S1), a fixed-size region cutout step (step S2), a down-sampling step (step S3), an up-sampling step (step S4), and a learning data storing step (step S5).

In step S1, the learning data generating unit 30 acquires the original real high resolution image ORH from the image storage unit 24. Here, the real high resolution image ORH equalized to the slice interval of 1 mm and the slice thickness of 1 mm is acquired.

In step S2, the fixed-size region cutout unit 31 performs processing of cutting out the fixed-size region from the input original real high resolution image ORH to generate the real high resolution image RH1 of the fixed-size region.

In step S3, the down-sampling processing unit 32 performs down-sampling of the real high resolution image RH1 to generate the thick slice image LK1. Here, as described with reference to FIG. 9, the thick slice image LK1 having the slice interval of 4 mm or 8 mm is generated.

In step S4, the up-sampling processing unit 34 performs up-sampling of the thick slice image LK1 obtained by the down-sampling to generate the low resolution image LQ1 corresponding to the low quality thin slice image. Here, as described with reference to FIG. 9, the interpolation processing and the Gaussian filter processing are performed by applying the slice interpolation magnification corresponding to the slice interval and the Gaussian filter conditions.

In step S5, the learning data generating unit 30 associates the low resolution image LQ1 generated in step S4 with the real high resolution image RH, which is the generation source data thereof, as an image pair, and stores these data in the learning data storage unit 38 as learning data.

After step S5, the learning data generating unit 30 completes the flowchart of FIG. 8.

In a case in which a plurality of pieces of the learning data are generated from the same original real high resolution image ORH by changing the location of the cutout region, after step S5, the process is returned to step S2, and the processes of steps S2 to S5 are repeated.

Further, in a case in which the low resolution images having different slice conditions or different assumed slice thicknesses are generated from the real high resolution image RH of the same fixed-size region, after step S5, the process is returned to step S3 or step S4, the processing condition is changed, and the process from step S3 or step S4 is repeated.

The learning data generating unit 30 can generate a large number of learning data by repeatedly executing the processes of steps S1 to S5 on a plurality of original real high resolution images stored in the image storage unit 24.

Learning Architecture

As described above, the generator 14 mounted on the super resolution image generating device 10 according to the present embodiment is the generative model acquired by performing learning by the GAN. The configuration and the learning method of the learning unit 40 will be described below in detail.

Figure 11:
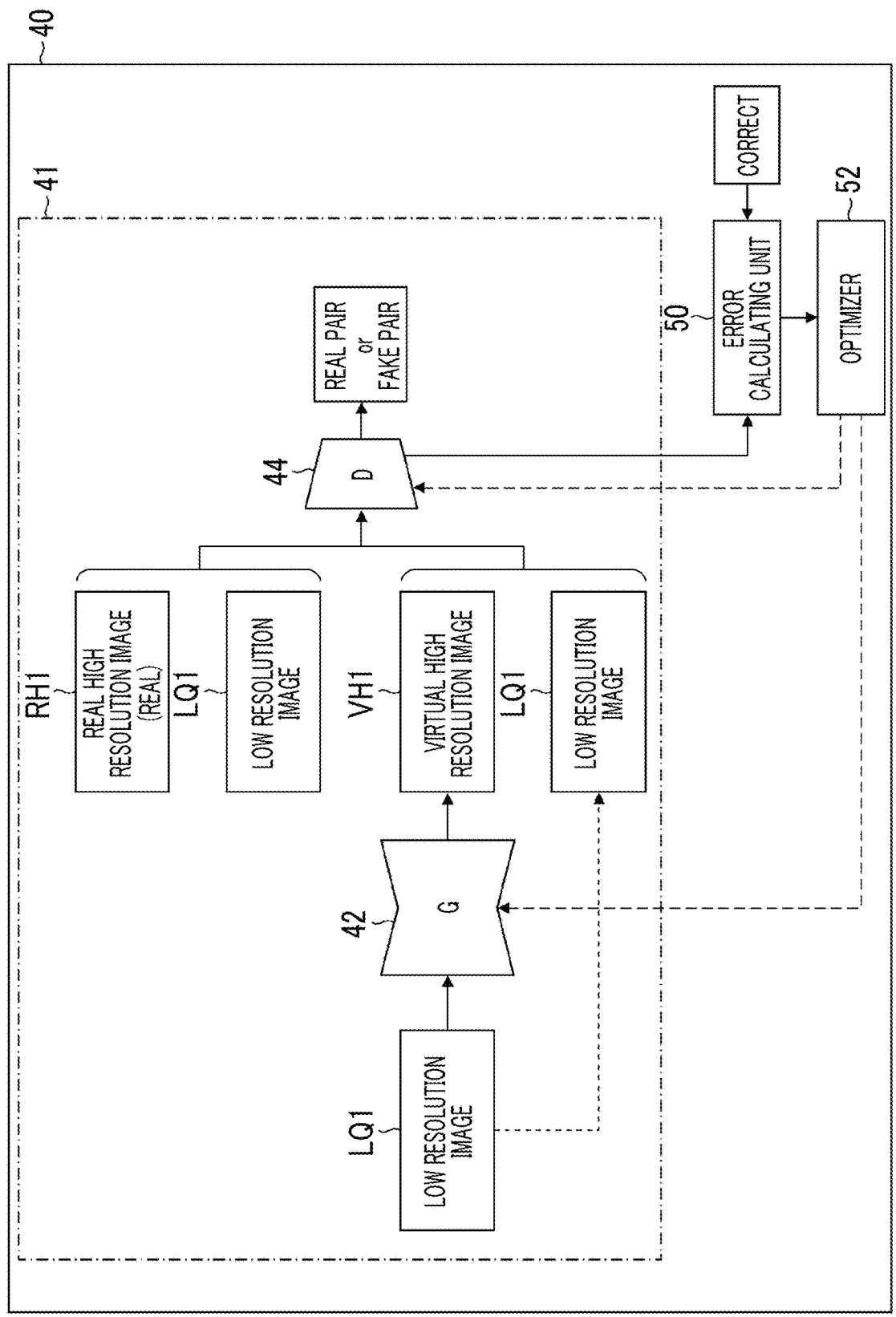
FIG. 11 is a conceptual diagram of processing in a learning unit to which a GAN is applied.

FIG. 11 is a conceptual diagram of processing in the learning unit 40 to which the GAN is applied. FIG. 11 shows an example in which a pair of the low resolution image LQ1 and the real high resolution image RH1 is input to the learning unit 40 as the data for learning.

The low resolution image LQ1 is the input to the generator 42G. The generator 42G generates a virtual high resolution image VH1 from the input low resolution image LQ1 and outputs the generated virtual high resolution image VH1. The virtual high resolution image VH1 corresponds to the virtual thin slice image (VTS image). A pair of the virtual high resolution image VH1 generated by the generator 42G and the low resolution image LQ1 which is the generation source of the virtual high resolution image VH1, or a pair of the real high resolution image RH1 which is the learning data and the low resolution image LQ1 is provided to be input to the discriminator 44D.

The discriminator 44D identifies whether the input image pair is a real pair including the real high resolution image RH1 (whether it is the learning data) or a fake pair including the virtual high resolution image VH1 derived from the output of the generator 42G, and outputs the identification result.

The error calculating unit 50 evaluates an error between the output of the discriminator 44D and the correct answer using the loss function. The optimizer 52 performs processing of automatically adjusting the network parameters based on the calculation result of the error calculating unit 50. The network parameters include the weight of connection between nodes and node bias. The optimizer 52 performs parameter calculation processing of calculating the update amount of the parameters of each network of the generator 42G and the discriminator 44D from the calculation result of the error calculating unit 50, and parameter update processing of updating the parameters of each network of the generator 42G and the discriminator 44D depending on the calculation result of the parameter calculation processing. The optimizer 52 updates the parameters based on the algorithm such as the gradient descent method. The technique disclosed in Ian J. Goodfellow, Jean Pouget-Abadie, Mehdi Mirza, Bing Xu, David Warde-Farley, Sherjil Ozair, Aaron Courville, Yoshua Bengio "Generative Adversarial Nets", arXiv: 1406.2661 or the like may be adopted for the part of the basic mechanism of learning regarding the error evaluation and the parameter update.

The generator 42G is learned to generate a more elaborate virtual high resolution image such that the discriminator 44D is deceived, and the discriminator 44D is learned to more accurately identify real or fake.

Finally, the portion of the generator 42G is used as the generator 14 which is the image generation module in the super resolution image generating device 10.

The self-attention mechanism is implemented in the network applied to the discriminator 44D according to the present embodiment. The self-attention mechanism is a method for improving calculation efficiency by considering a wide part in the image.

Explanation of Discriminator 44D Including Self-Attention Mechanism

The content of the self-attention mechanism is disclosed in Han Zhang, Ian Goodfellow, Dimitris Metaxas, Augustus Odena "Self-Attention Generative Adversarial Networks", arXiv: 1805.08318. However, the present embodiment is different from the method disclosed in Han Zhang, Ian Goodfellow, Dimitris Metaxas, Augustus Odena "Self-Attention Generative Adversarial Networks", arXiv: 1805.08318 in that the self-attention mechanism is added to both networks of the generator and discriminator in Han Zhang, Ian Goodfellow, Dimitris Metaxas, Augustus Odena "Self-Attention Generative Adversarial Networks", arXiv: 1805.08318, whereas the self-attention mechanism is not implemented in the generator 42G, and the self-attention mechanism is implemented in only the discriminator 44D in the present embodiment.

The self-attention mechanism will be briefly outlined with reference to the contents of Han Zhang, Ian Goodfellow, Dimitris Metaxas, Augustus Odena "Self-Attention Generative Adversarial Networks", arXiv: 1805.08318. The self-attention mechanism generates a query $f(x)$ and a key $g(x)$ from the convolutional feature map $CFM(x)$ output from the hidden layer of the previous layer, and uses these query and key to calculate a value (similarity), which indicate which other pixel is similar, for each pixel. The map of similarity calculated as described above, which corresponds to all pixels of the feature map $CFM(x)$ is called an "attention map".

The attention map serves to find and emphasize regions having similar features in the image. In the convolutional calculation of the convolutional layer that configures the identification network, local information is superimposed, but by introducing the attention map, it is possible to consider the information of the wide (overall) part.

This attention map is multiplied by a weight $h(x)$ to obtain a self-attention feature map $SAFM(o)$. Then, the self-attention feature map $SAFM(o)$ is multiplied by a scale parameter $\gamma$, added to the convolutional feature map $CFM(x)$ which is the original input feature map, and passed to the next layer.

That is, a final output y to be passed to the next layer is obtained by the following equation.

$$y = \gamma \cdot o + x$$

In the network of the discriminator 44D which includes such a self-attention mechanism, the parameters of f(x), g(x), and h(x) of the self-attention mechanism are also learned.

Example of Identification Network

Figure 12:
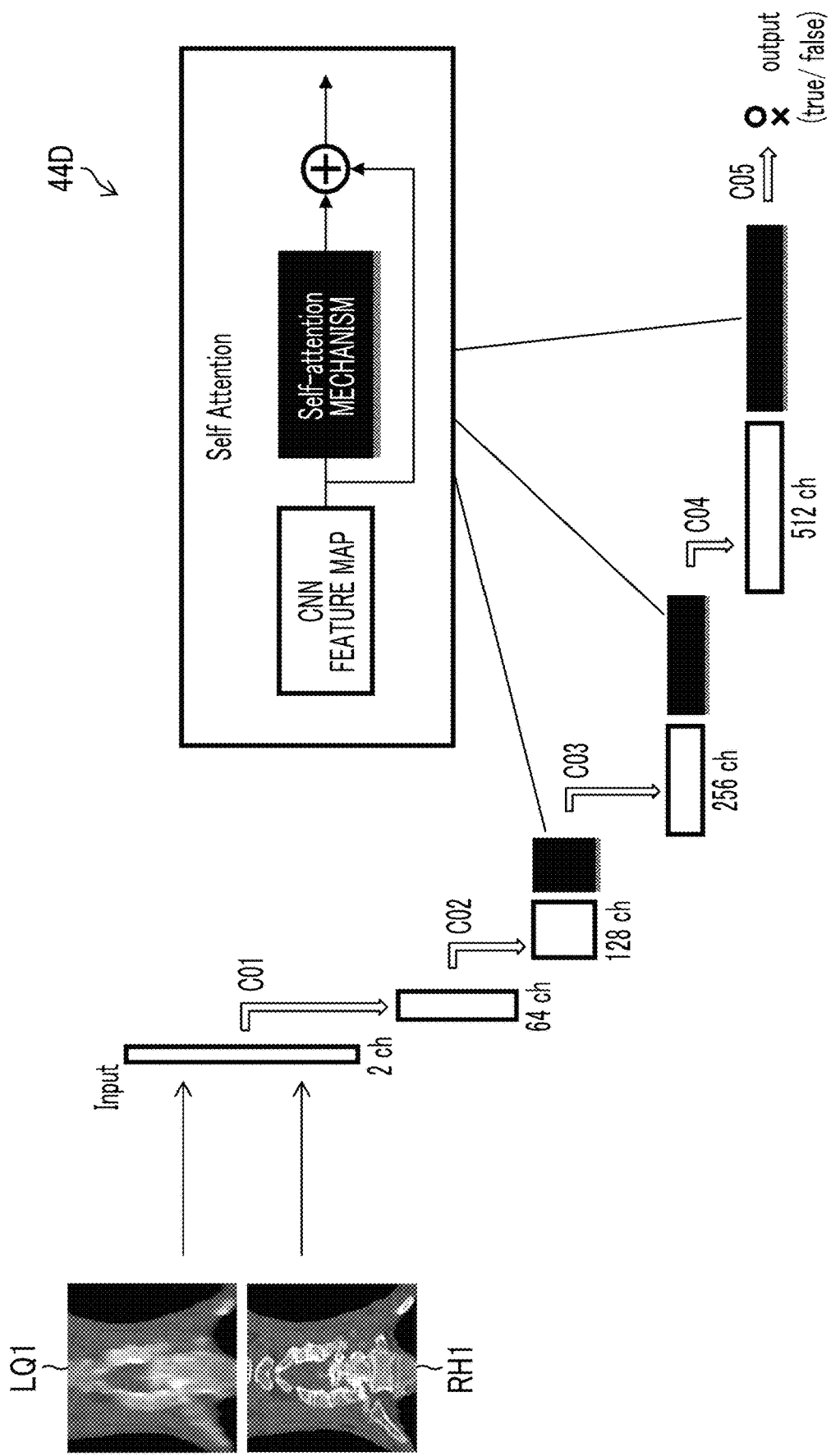
FIG. 12 is a conceptual diagram showing an example of an identification network applied to a discriminator.

FIG. 12 is a conceptual diagram showing an example of the identification network applied to the discriminator 44D. The network of the discriminator 44D is a multilayered neural network classified as a deep neural network, and includes a plurality of convolutional layers. The network of the discriminator 44D is configured by a convolutional neural network (CNN).

In FIG. 12, the white arrows indicated by the reference numerals C01, C02 . . . C05 represent the "convolutional layers". The rectangles shown on the input side and/or output side of each layer represent a set of feature maps. The length of the rectangle in the vertical direction represents the size (number of pixels) of the feature map, and the width of the rectangle in the horizontal direction represents the number of channels. In the discriminator 44D of this example, a pooling layer is not present, and for example, by convolving the filter having a size of 4×4×4 with stride=2, the image size of the feature map is reduced. For example, in a case in which the CNN processing is performed, the minimum image size after convolution can be 1/16 of the size of the input data.

In the example shown in FIG. 12, the self-attention mechanism is introduced from the convolutional layer C02 to each of the subsequent layers. For example, the self-attention feature map is generated for each of CNN feature map of 128 channel output from the convolutional layer C02. FIG. 12 shows that the self-attention feature maps of the 128 channel corresponding to the CNN feature maps of the 128 channel are added. Each of the CNN feature map and the self-attention feature map is added for each channel, and the output is input to the next convolutional layer. The same applies to the convolutional layers C03 and C04.

The CNN feature map to be input to the self-attention mechanism is calculated by converting the entire image to be input into the one-dimensional array. The CNN feature map in which the number of input channels is C and the total number of pixels is N is input to the self-attention mechanism as a vector in which C×N elements of each pixel are arranged one-dimensionally.

The actual CT image data is the three-dimensional data, and the multidimensional data can be calculated as the one-dimensional array in the same manner as described above. The same processing algorithm can be applied to both the two-dimensional image data and the three-dimensional image data by calculating the data as the one-dimensional array.

Example of Generation Network

Figure 13:
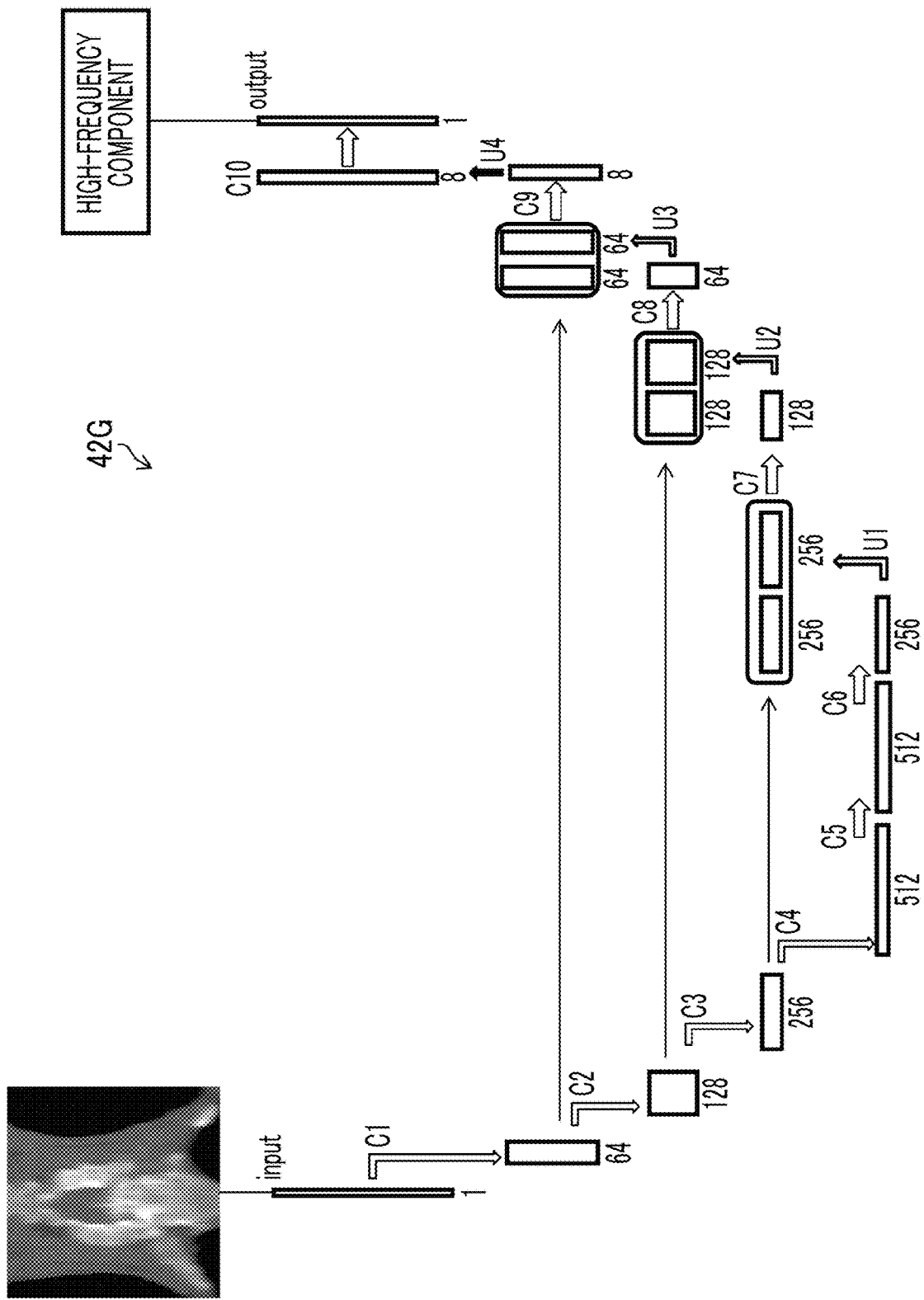
FIG. 13 is a conceptual diagram showing an example of a generation network applied to a generator.

FIG. 13 is a conceptual diagram showing an example of the generation network applied to the generator 42G. The network of the generator 42G is also configured by a convolutional neural network. The generator 42G preferably has a configuration with an encoder and decoder structure in which an encoder portion and a decoder portion are combined. An example of a U-shaped network called a U-Net structure is shown in FIG. 13. "Net" in the notation of "U-Net" is a simple notation of "network".

In FIG. 13, the arrows indicated by the reference numerals C1, C2 . . . C10 each represent the "convolutional layers". The arrows, which are indicated by the reference numerals U1, U2, U3, and U4, represent the convolutional layers that perform "convolution and up-sampling". Similar to the discriminator 44D described with reference to FIG. 12, in the generator 42G shown in FIG. 13, a pooling layer is not present, and by convolving the filter with stride=2, the image size of the feature map is reduced in the encoder portion.

Figure 14:
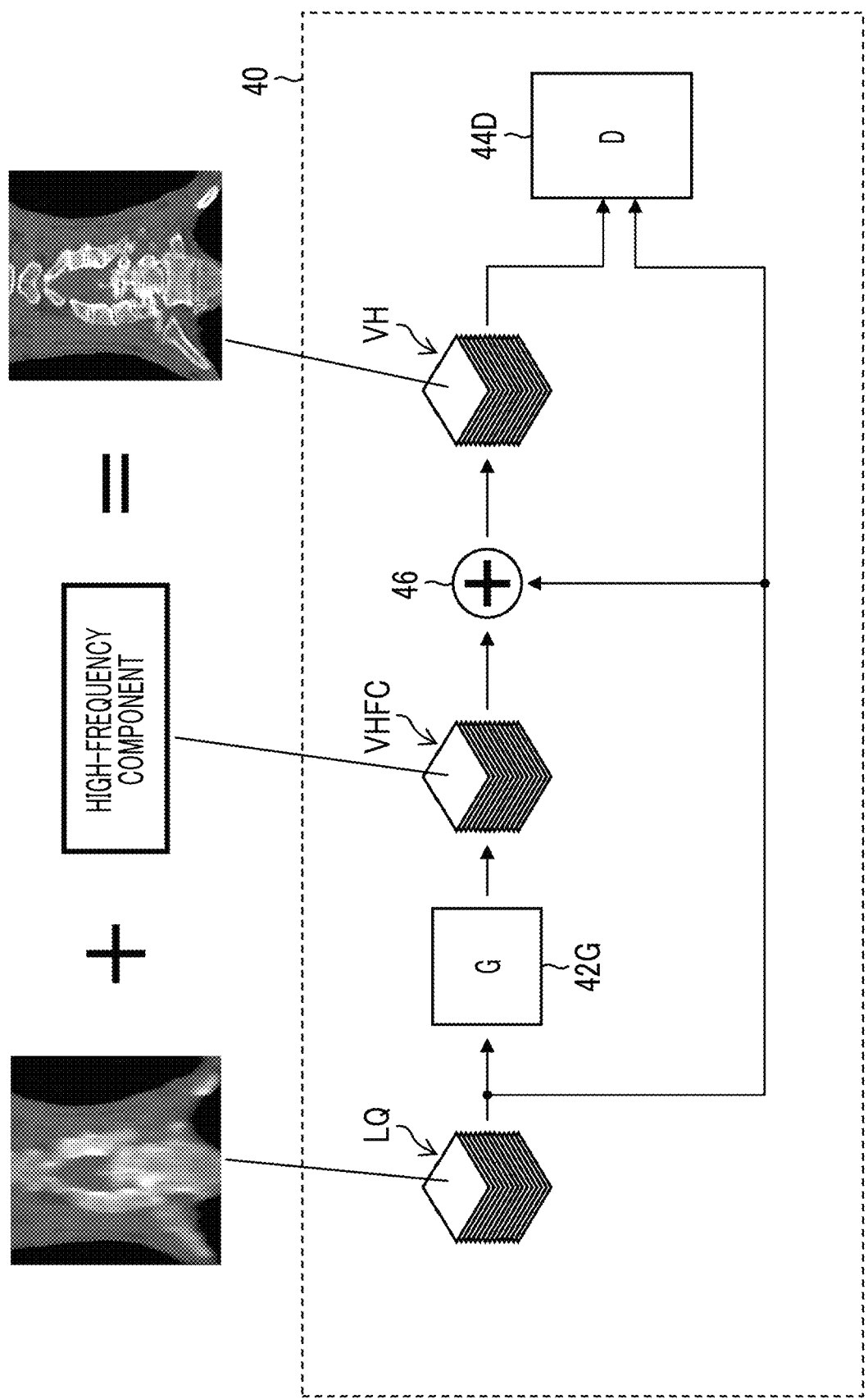
FIG. 14 is an explanatory diagram of an operation of adding a low resolution image to the output of the generator to generate a virtual high resolution image.

The generator 42G estimates a high-frequency component image VHFC as the high resolution information required for the increase in a resolution from the input low resolution image LQ and outputs the estimated high-frequency component image VHFC. As shown in FIG. 14, a virtual high resolution image VH is obtained by adding the low resolution image LQ which is the input data to the generator 42G and the high-frequency component image VHFC generated by the generator 42G. The slice interval and the slice thickness of the virtual high resolution image VH1 are the same as the slice interval and the slice thickness of the low resolution image LQ1, but the virtual high resolution image VH1 is an image sharper in the Z direction as compared with the low resolution image LQ1.

The learning unit 40 comprises an addition unit 46 that adds the input of the generator 42G and the output of the generator 42G, and has a configuration in which the output of the addition unit 46 is input to the discriminator 44D. The addition unit 46 is an example of a "second addition unit" in the present disclosure. The addition unit 46 is not shown in FIGS. 7 and 11. The virtual high resolution image VH1 input to the discriminator 44D is an example of a "virtual second image" in the present disclosure.

The low resolution image LQ provided as the input to the generator 42G is an example of a "first image" in the present disclosure. The high-frequency component image output from the generator 42G is an example of a "second image" in the present disclosure.

In FIGS. 13 and 14, an example in which the output of the generator 42G is the high-frequency component image VHFC is described, a form in which the output of the generator 42G is the virtual high resolution image VH can be adopted. In this case, the addition unit 46 is unnecessary. Such an embodiment will be described below as a second embodiment.

Identification Operation of Discriminator 44D at Time of Learning

Figure 15:
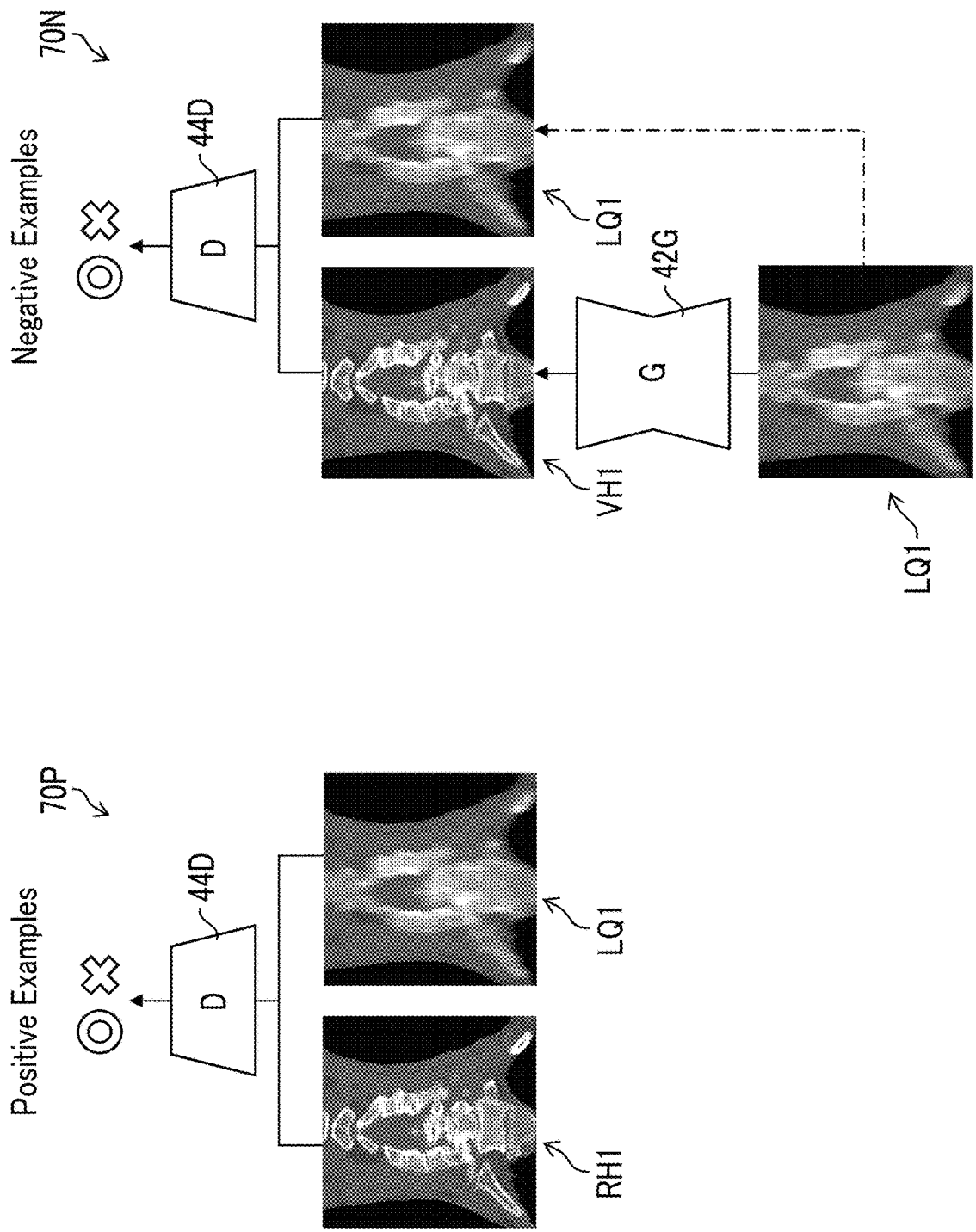
FIG. 15 is a diagram for explaining an operation of identification by the discriminator at the time of learning.

FIG. 15 is a diagram for explaining an operation of identification by the discriminator 44D at the time of learning. The addition unit 46 is not shown in FIG. 15.

An operation state 70P shown on the left side of FIG. 15 indicates a case in which a positive sample (positive example) is input to the discriminator 44D, an operation state 70N shown on the right side of FIG. 15 indicates a case in which a negative sample (negative example) is input to the discriminator 44D.

This is an example in which the real high resolution image RH1 and the low resolution image LQ1 corresponding to the real high resolution image RH1, which are an image pair of learning data, are input. In this case, in a case in which the discriminator 44D identifies the input high resolution image as the real high resolution image RH1, the output (identification result) of the discriminator 44D is correct, and in a case in which the discriminator 44D identifies the input high resolution image as the virtual high resolution image VH1, identification result is incorrect.

On the other hand, in the case of the operation state 70N shown on the right side of FIG. 15, the image pair of the virtual high resolution image VH1 derived from the generator 42G and the low resolution image LQ1 which is the generation source data thereof is input to the discriminator 44D. In this case, in a case in which the discriminator 44D identifies the input high resolution image as the real high resolution image RH1, the identification result is incorrect, and in a case in which the discriminator 44D identifies the input high resolution image as the virtual high resolution image VH1, the identification result is correct.

The discriminator 44D is learned to make the identification correct as to whether the input high resolution image is the real CT image captured by the CT device (not shown) or the virtual CT image generated by the generator 42G. On the other hand, the generator 42G is learned to generate the virtual CT image resembling the real CT image captured by the CT device (not shown) and to make the identification of the discriminator 44D incorrect.

As the learning progresses, the discriminator 44D and the generator 42G increase each other's accuracy, and the generator 42G can generate the virtual high resolution image VH close to the real CT image, which is not identified as a fake (virtual high resolution image) by the discriminator 44D.

The learned generator 42G acquired by such learning is applied as the generator 14 of the super resolution image generating device 10 described with reference to FIG. 6.

Learning Method Using Learning System 20

Figure 16:
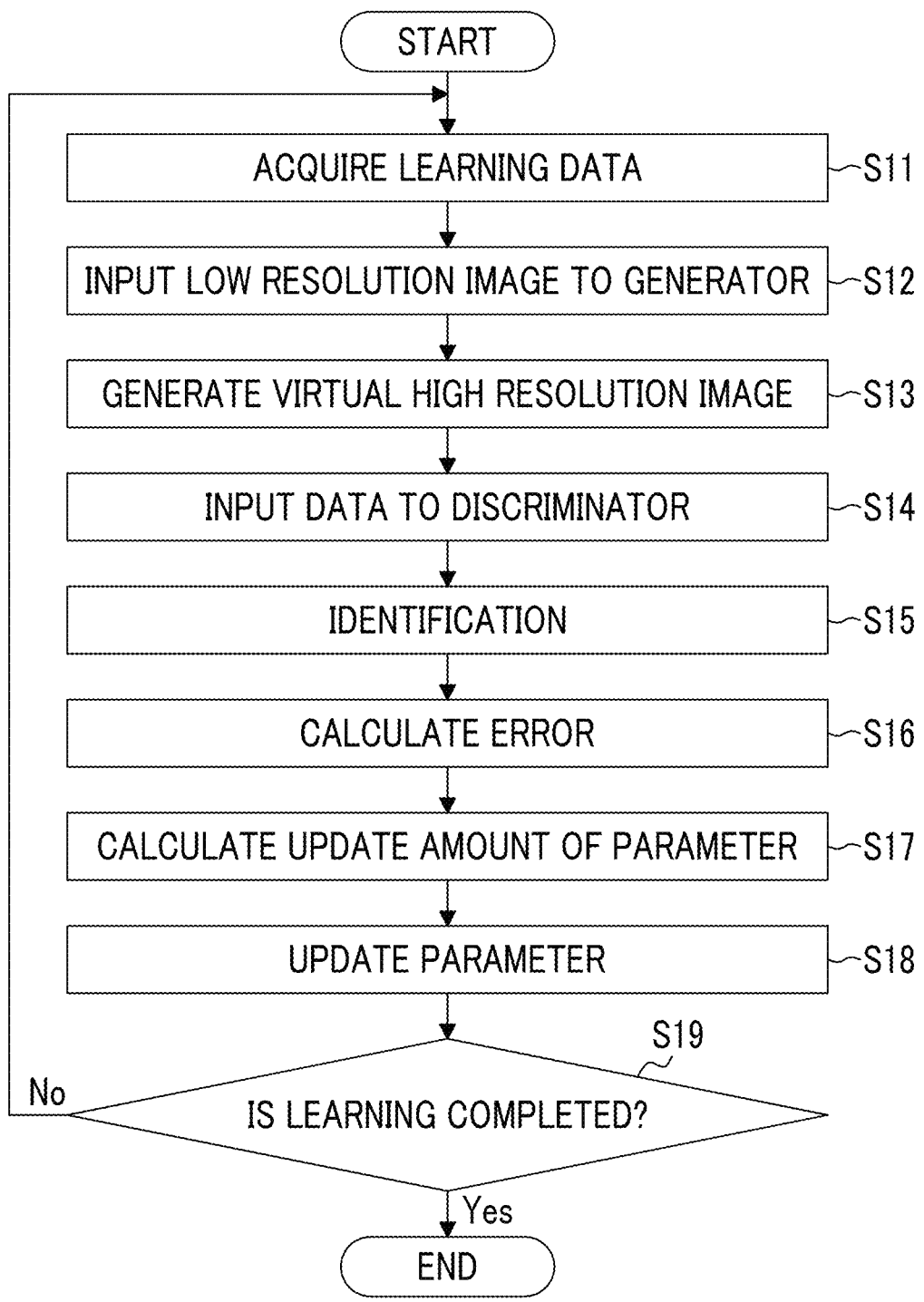
FIG. 16 is a flowchart showing an example of a procedure for processing in the learning unit.

FIG. 16 is a flowchart showing an example of a procedure for processing in the learning unit 40. Each step of the flowchart shown in FIG. 16 is executed by a computer including a processor that functions as the learning unit 40.

The learning unit 40 acquires the learning data in step S11. The learning unit 40 reads the learning data from the learning data generating unit 30 described with reference to FIG. 8. The learning unit 40 can acquire the learning data in a unit of mini batch including a plurality of pieces of the learning data.

The learning unit 40 inputs the low resolution image of the learning data to the generator 42G in step S12.

The generator 42G generates the virtual high resolution image from the input low resolution image in step S13. The output from the generator 42G may be the high-frequency component image VHFC required to produce the virtual high resolution image. In this case, as described with reference to FIG. 14, the high-frequency component image VHFC and the low resolution image are added to generate the virtual high resolution image VH.

The learning unit 40 inputs the data to the discriminator 44D in step S14. As the input to the discriminator 44D, any of a pair (real pair) of the learning data including the real high resolution image as the correct image or a fake pair including the virtual high resolution image derived from the generator 42G is selectively provided.

The discriminator 44D identifies the data in step S15.

The error calculating unit 50 calculates the error of the identification result and sends the calculation result to the optimizer 52 in step S16.

The optimizer 52 calculates the update amount of the network parameters based on the calculated error in step S17.

In step S18, the optimizer 52 performs parameter update processing depending on the update amount of the parameters calculated in step S17. The parameter update processing is performed in a unit of mini batch.

The learning unit 40 determines whether or not to complete the learning in step S19. A learning completing condition may be determined based on the error value or may be determined based on the number of updates of parameter. As the method based on the error value, for example, the learning completing condition may be that the error converges within a specified range. As the method based on the number of updates, for example, the learning completing condition may be that the number of updates reaches the specified number of times.

In a case in which the determination result in step S19 is No, the learning unit 40 returns the process to step S11 and repeats the learning processing until the learning completing condition is satisfied.

In a case in which the determination result in step S19 is Yes, the learning unit completes the flowchart of FIG. 16.

The portion of the learned generator 42G obtained as described above is applied as the generator 14 of the super resolution image generating device 10.

Effect of First Embodiment

Figure 17:
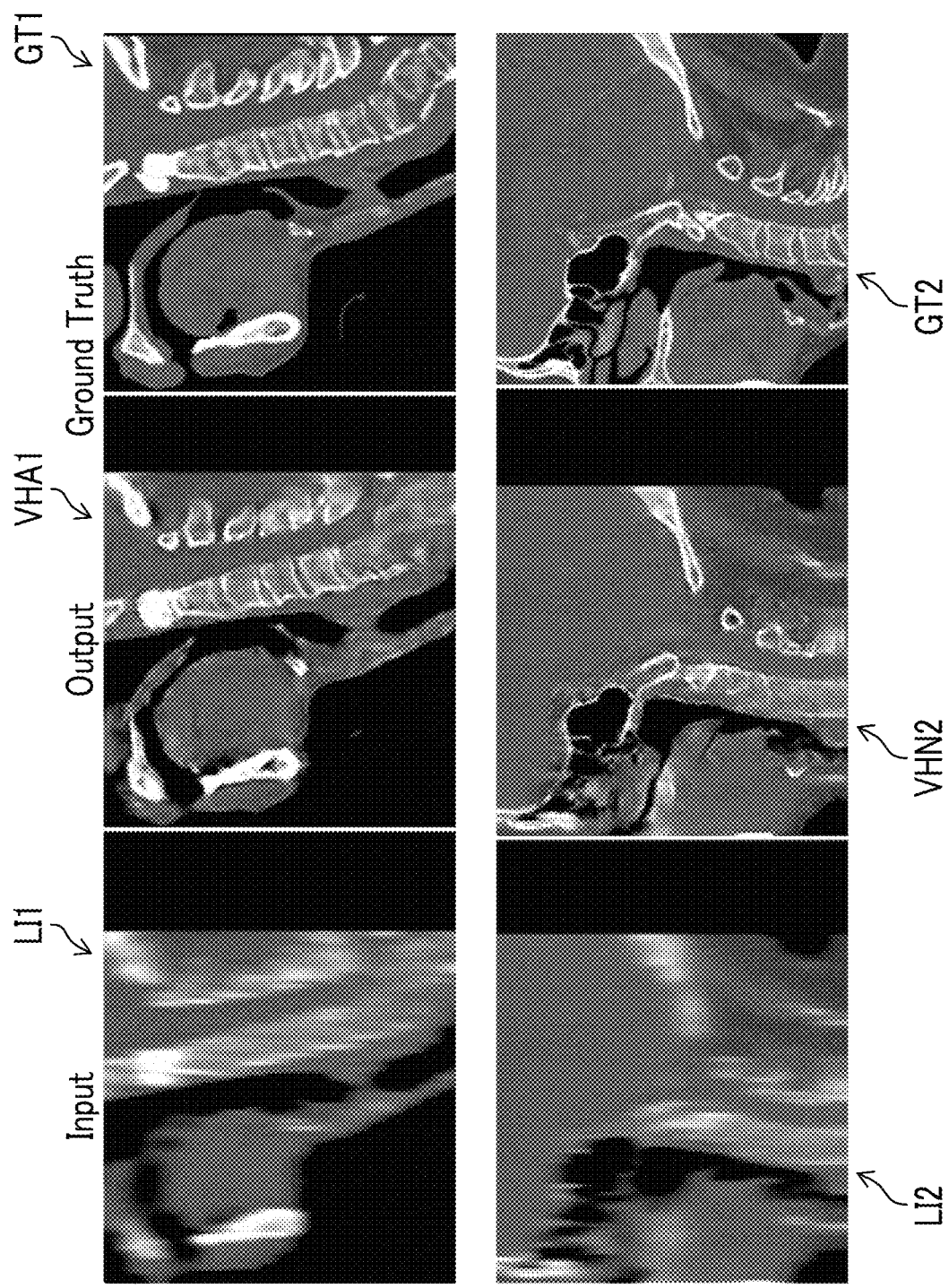
FIG. 17 is an example of an image, which shows the effect of the embodiment.

FIG. 17 is an example of an image, which shows the effect of the present embodiment. FIG. 17 shows an example of an image, which shows the effect of introducing the self-attention mechanism. An image VHA1 shown in the upper center of FIG. 17 is an example of the virtual high resolution image generated by using the learned model (generator 14) to which the learning method according to the present embodiment is applied. An image LI1 shown on the upper left of FIG. 17 is an example of the low resolution image used for input to the generator 14. An image GT1 shown on the upper right of FIG. 17 is the correct image (ground truth) corresponding to the input image LI1.

An image VHN2 shown in the lower center of FIG. 17 is an example of the virtual high resolution image generated by using the learned model according to Comparative Example. The learned model according to Comparative Example is learned by using the discriminator that does not include the attention mechanism. An image LI2 shown on the lower left of FIG. 17 is an example of the low resolution image used for input to the learned model according to Comparative Example. An image GT2 shown on the lower right of FIG. 17 is the correct image (ground truth) corresponding to the input image LI2.

The image VHA1 shown in the upper center of FIG. 17 is the image very close to the correct image GT1. Further, it can be seen that the image VHA1 reduces the local noise as compared with the image VHN2 in Comparative Example on the lower side of FIG. 17.

That is, according to the present embodiment, the noise locally generated in Comparative Example can be reduced by the effect of introducing the self-attention mechanism into the discriminator 44D.

Figure 18:
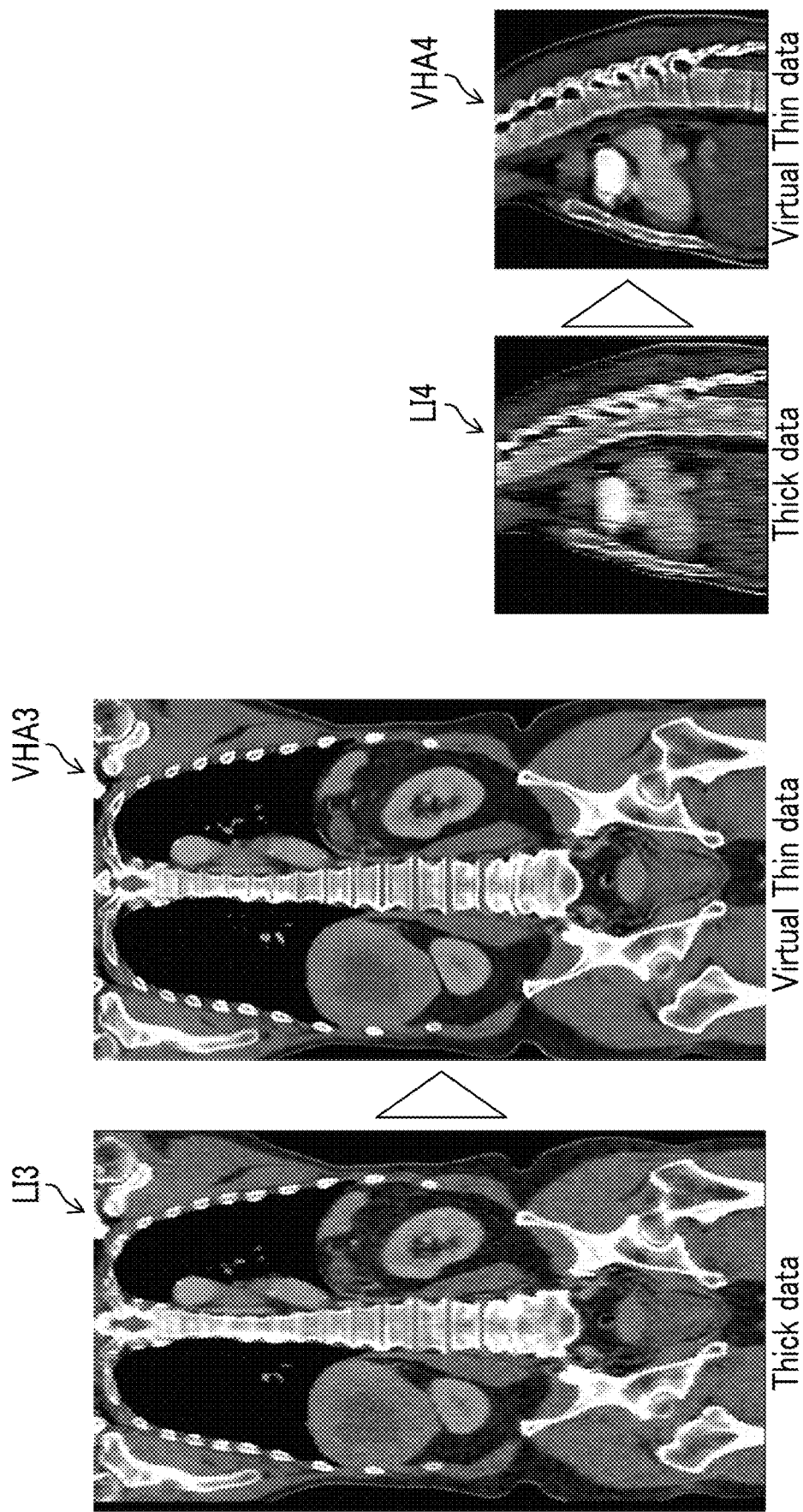
FIG. 18 is a diagram for explaining other effects of the embodiment.

FIG. 18 is a diagram for explaining other effects of the present embodiment. FIG. 18 shows an image example showing that the learned model (generator 14) to which the learning method according to the present embodiment is applied can execute image generation processing (super resolution processing) regardless of the input size.

An image LI3 shown on the far left of FIG. 18 is an example of an image input to the learned model (generator 14) to which the learning method according to the present embodiment is applied. An image VHA3 which is second from the left in FIG. 18 is an example of the virtual high resolution image generated by using the generator 14 from the input of the image LI3.

An image LI4 which is third from the left in FIG. 18 is another example of the image input to the generator 14. This image LI4 has a smaller image size than the image LI3 shown on the far left of FIG. 18. An image VHA4 shown on the far right of FIG. 18 is an example of the virtual high resolution image generated by using the generator 14 from the input of the image LI4.

As shown in FIG. 18, the generator 14 can also perform the estimation processing on the input of the image having a size different from the image size used at the time of learning. The generator 14 can generate the image with high accuracy for the input data of any image size. That is, according to the present embodiment, the image generation processing can be performed on the image of any size without being restricted by the image size, which is the fixed size, used as the learning data at the time of learning. According to the present embodiment, the processing can be performed by dividing the input data into memories of any size.

Since the discriminator 44D is only used in a case of learning and does not need to be mounted on the super resolution image generating device 10, learning is performed with the fixed size even in a case in which the attention mechanism is added to the discriminator 44D, and there is no problem.

Modification Example

In the first embodiment described above, the pair of the real high resolution image RH and the low resolution image LQ1 or the pair of the virtual high resolution image VH derived from the generator 42G and the low resolution image LQ1 is provided as the input to the discriminator 44D, but it is not essential to input the low resolution image LQ1 to the discriminator 44D. At least the real high resolution image RH or the virtual high resolution image VH need only be input to the discriminator 44D.

Second Embodiment

In the first embodiment, as shown in FIG. 14, the virtual high resolution image VH is obtained by outputting the (virtual) high-frequency component image VHFC from the generator 42G and adding the low resolution image LQ and the high-frequency component image VHFC. On the other hand, in the second embodiment, the generator 42G outputs the virtual high resolution image VH.

Figure 19:
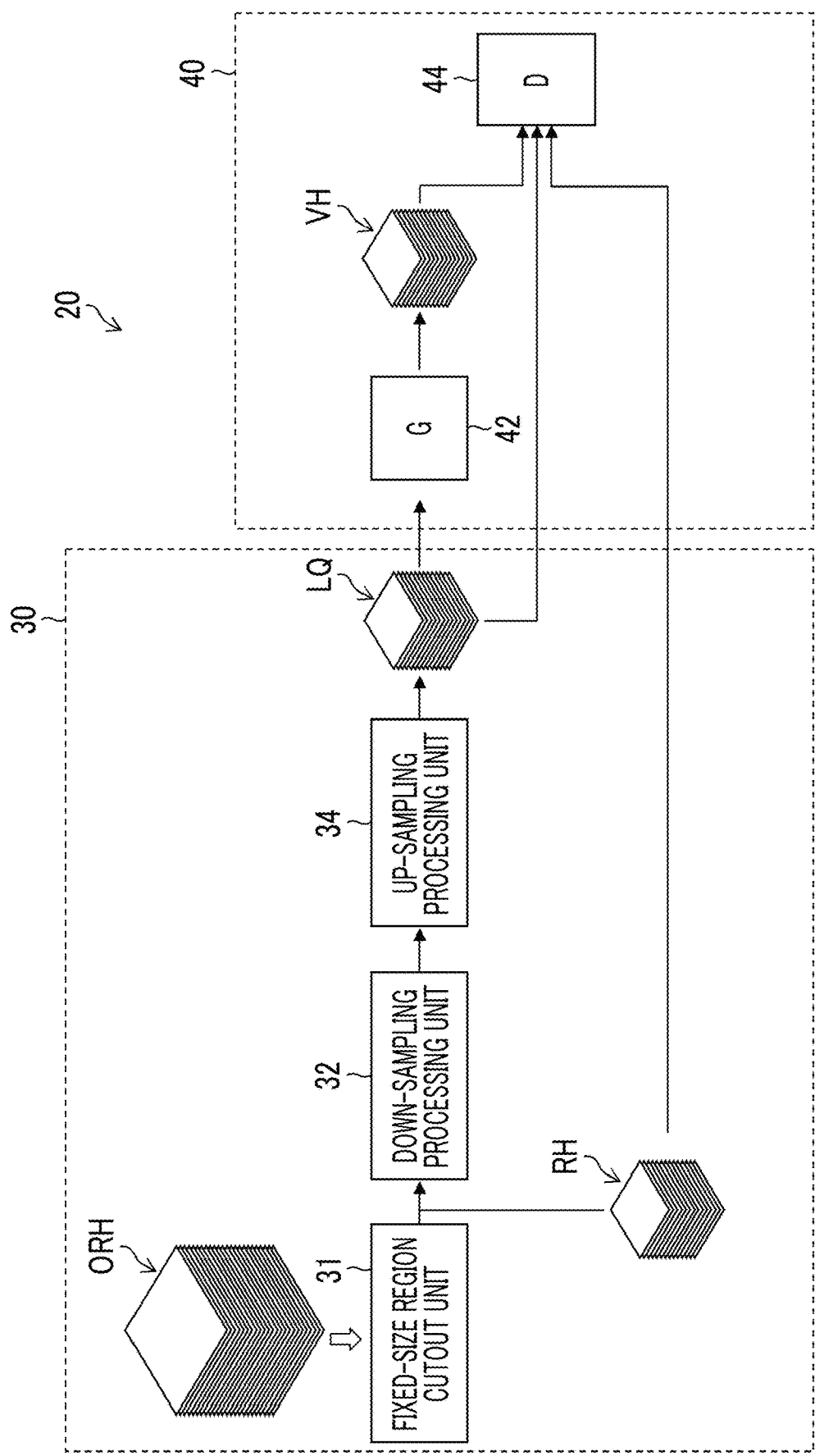
FIG. 19 is a functional block diagram schematically showing a flow of processing by the learning system according to a second embodiment.

FIG. 19 is a functional block diagram schematically showing a flow of the processing by the learning system 20 according to the second embodiment. In FIG. 19, the portions common to or similar to the configurations shown in FIGS. 7, 8, and 11 to 14 are designated by the same reference numerals, and detailed description thereof will be omitted.

In FIG. 19, the content of the learning data generating unit 30 is the same as that in FIG. 8. The generator 42G of the learning unit 40 according to the second embodiment generates the virtual high resolution image VH1 from the low resolution image LQ1.

Also, the low resolution image LQ1 is input to the discriminator 44D in a pair with the real high resolution image RH1 or the virtual high resolution image VH1. The discriminator 44D identifies whether the input image is the real high resolution image RH1 or the virtual high resolution image VH1. The low resolution image LQ1 may not be input to the discriminator 44D.

According to the second embodiment, it is possible to obtain the generative model (generator 42G) that generates the virtual high resolution image VH1 from the low resolution image LQ1. In a case in which the generator 42G generated in the second embodiment is incorporated in the super resolution image generating device 10, the addition unit 16 shown in FIG. 6 can be omitted.

Third Embodiment

Figure 20:
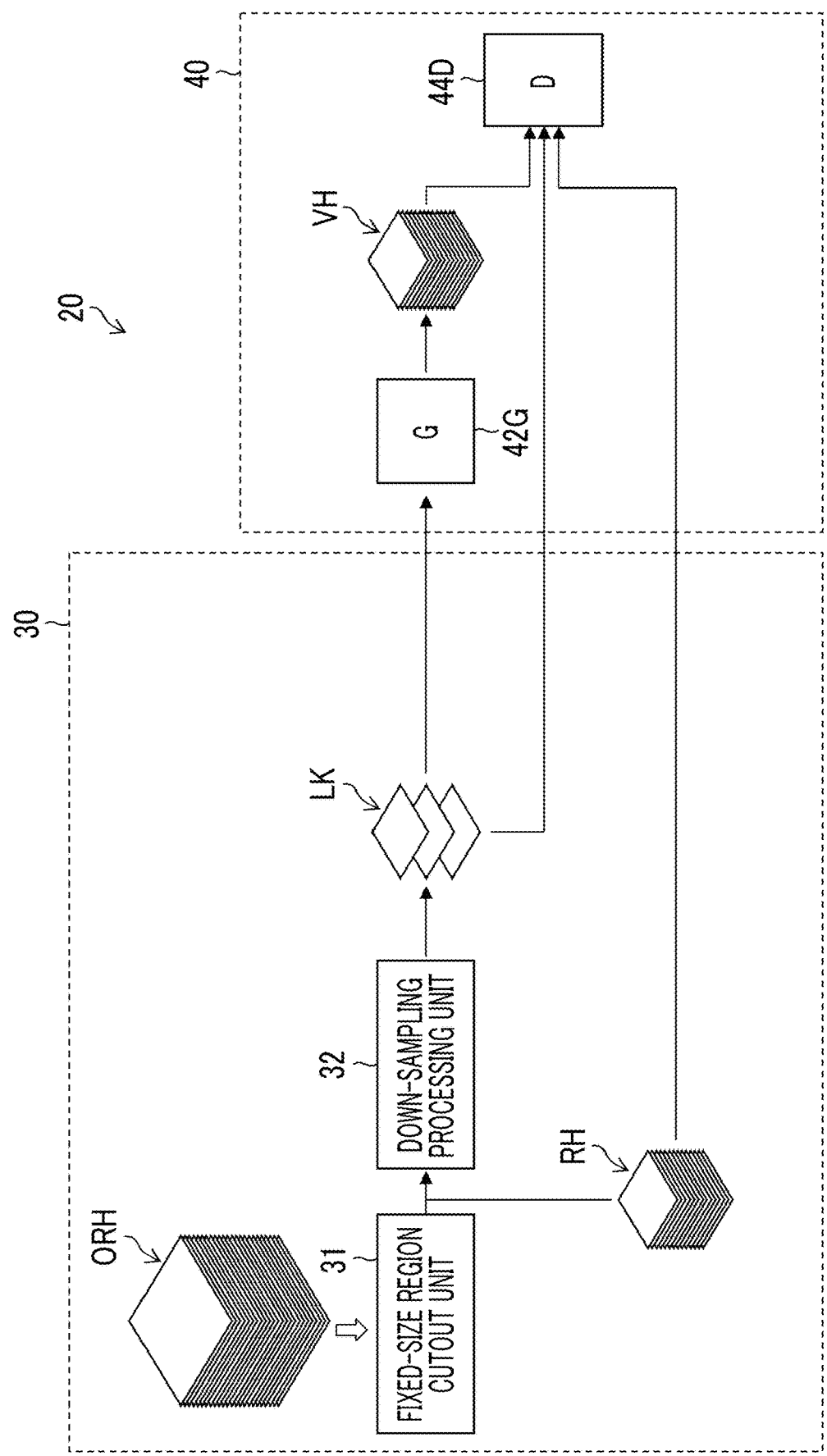
FIG. 20 is a functional block diagram schematically showing a flow of processing by the learning system according to a third embodiment.

FIG. 20 is a functional block diagram schematically showing a flow of processing by the learning system 20 according to a third embodiment. In FIG. 20, the portions common to or similar to the configurations shown in FIG. 19 are designated by the same reference numerals, and detailed description thereof will be omitted. In the third embodiment shown in FIG. 20, the input to the generator 42G is a thick slice image LK, and the output from the generator 42G is the virtual high resolution image VH. In this case, the pair of the thick slice image LK and the real high resolution image RH is the learning data. In FIG. 20, the thick slice image LK is an example of the "first image" and the "first learning image" in the present disclosure.

According to the third embodiment, the generator 42G is learned to generate the virtual high resolution image VH1 from the thick slice image LK. Therefore, by performing the learning of the third embodiment, it is possible to obtain the generative model (generator 42G) that generates the virtual high resolution image VH1 from the thick slice image LK.

Fourth Embodiment

Figure 21:
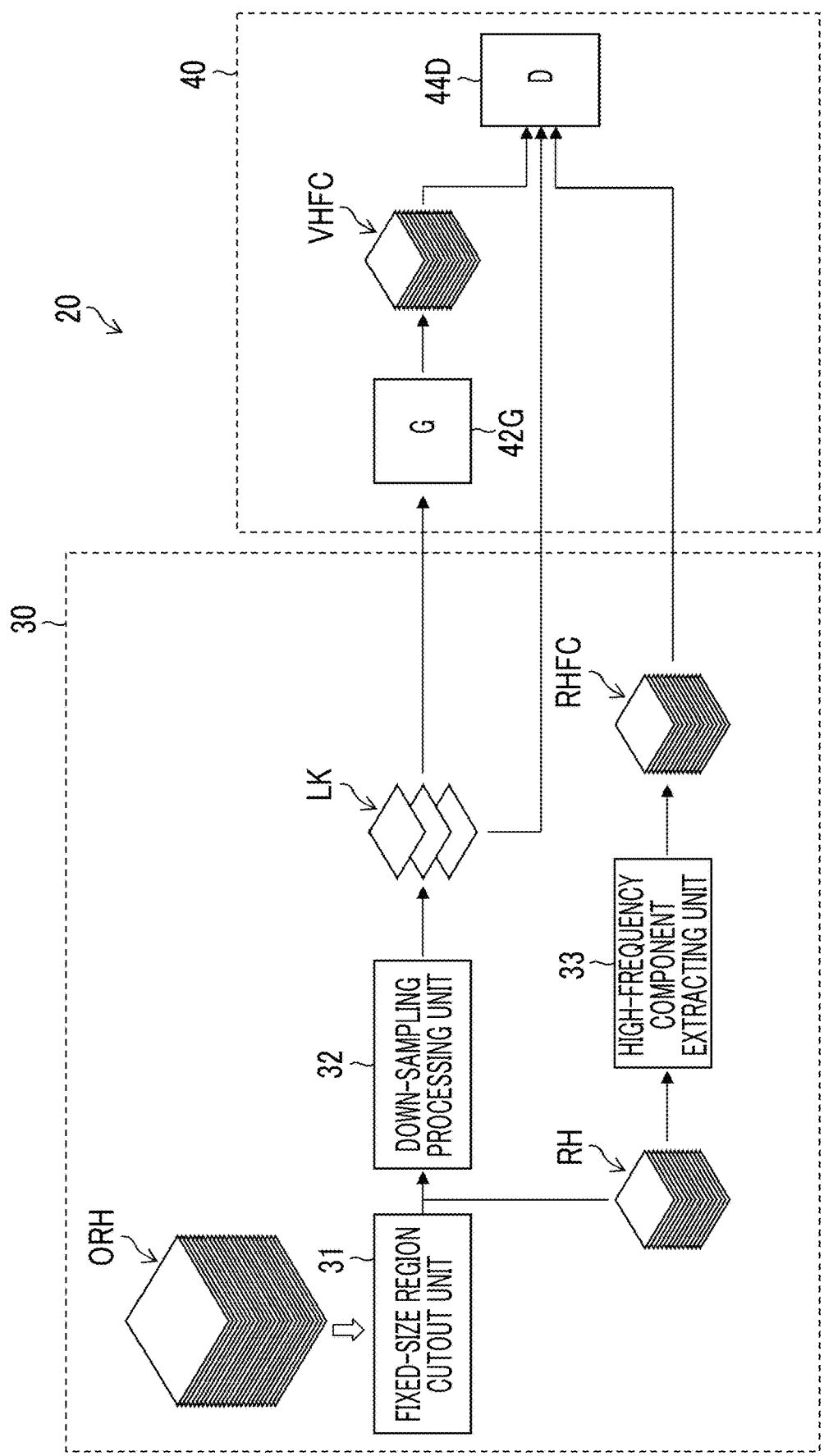
FIG. 21 is a functional block diagram schematically showing a flow of processing by the learning system according to a fourth embodiment.

FIG. 21 is a functional block diagram schematically showing a flow of processing by the learning system 20 according to a fourth embodiment. In FIG. 21, the portions common to or similar to the configurations shown in FIG. 19 are designated by the same reference numerals, and detailed description thereof will be omitted. The learning system 20 according to the fourth embodiment shown in FIG. 21 inputs the thick slice image LK to the generator 42G, outputs the high-frequency component image VHFC from the generator 42G, inputs the high-frequency component image to the discriminator 44D, and performs the identification. The learning data generating unit 30 comprises a high-frequency component extracting unit 33 in order to produce the high-frequency component image for learning used for input of the discriminator 44D.

The high-frequency component extracting unit 33 extracts the high-frequency components from the real high resolution image RH and generates a real high-frequency component image RHFC. Extraction of the high-frequency components is performed by using a high-pass filter. Similar to the real high resolution image RH, the real high-frequency component image RHFC has the slice interval of 1 mm and the slice thickness of 1 mm.

In the fourth embodiment, a pair of the thick slice image LK and the real high-frequency component image RHFC is the learning data. In FIG. 21, the real high-frequency component image RHFC is an example of the "second learning image" in the present disclosure.

The real high-frequency component image RHFC generated by the high-frequency component extracting unit 33 is input to the discriminator 44D of the learning unit 40.

The generator 42G of the learning unit 40 generates a virtual high-frequency component image VHFC having the same resolution as the real high-frequency component image RHFC from the input thick slice image LK. Here, the generator 42G generates the virtual high-frequency component image VHFC having the slice interval of 1 mm and the slice thickness of 1 mm.

The pair of the real high-frequency component image RHFC and the thick slice image LK or the pair of a virtual high resolution image VHFC derived from the output of the generator 42G and the thick slice image LK is input to the discriminator 44D.

The discriminator 44D identifies whether the input high-frequency component image is the real high-frequency component image RHFC or the virtual high-frequency component image VHFC.

According to the fourth embodiment, the generator 42G is learned to generate the high-frequency component image from the thick slice image LK which is the low resolution image. As described with reference to FIG. 14, the high resolution image can be obtained by adding processing of the high-frequency component image generated by the generator 42G and the thick slice image LK which is the input of the generator 42G.

Example of Hardware Configuration of Computer

Figure 22:
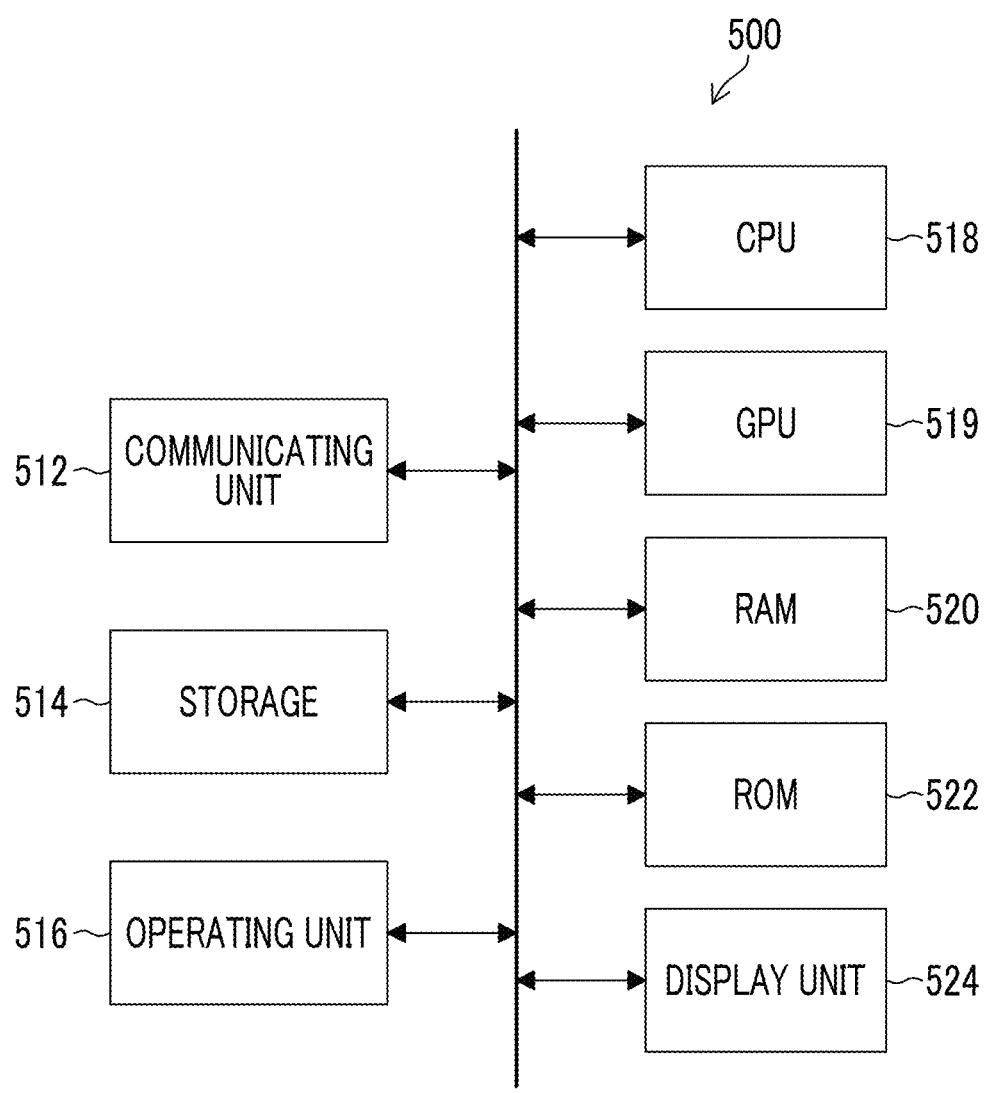
FIG. 22 is a block diagram showing an example of a computer hardware configuration.

FIG. 22 is a block diagram showing an example of a computer hardware configuration, which is used in the learning system 20. A computer 500 may be a personal computer, may be a workstation, or may be a server computer. The computer 500 can be used as any one of the super resolution image generating device 10, the image storage unit 24, the learning data generating unit 30, and the learning unit 40, or a device having a plurality of functions thereof.

The computer 500 comprises a communicating unit 512, a storage 514, an operating unit 516, a central processing unit (CPU) 518, a graphics processing unit (GPU) 519, a random access memory (RAM) 520, a read only memory (ROM) 522, and a display unit 524. The graphics processing unit (GPU) 519 may be omitted.

The communicating unit 512 is an interface that performs communication processing with an external device by wire or wirelessly and exchanges information with the external device.

The storage 514 is configured to include, for example, a hard disk apparatus, an optical disk, a magneto-optical disk, or a semiconductor memory, or a storage device configured by using an appropriate combination thereof. The storage 514 stores various programs, data, and the like required for the image processing such as the learning processing and/or the image generation processing. The program stored in the storage 514 is loaded into the RAM 520, and the CPU 518 executes the program, so that the computer functions as means for performing various processing specified by the program.

The operating unit 516 is an input interface that receives various operation inputs with respect to the computer 500. The operating unit 516 may be, for example, a keyboard, a mouse, a touch panel, an operation button, a voice input device, or an appropriate combination thereof.

The CPU 518 reads out various programs stored in the ROM 522, the storage 514, and the like, and executes various processing. The RAM 520 is used as a work region of the CPU 518. Further, the RAM 520 is used as a storage unit that temporarily stores the read program and various data.

The display unit 524 is an output interface on which various types of information are displayed. The display unit 524 may be, for example, a liquid crystal display, an organic electro-luminescence (OEL) display, a projector, or an appropriate combination thereof.

About Program Causing Computer to Operate

The program that causes the computer to realize a part or all of at least one processing functions among the learning data generation function, the learning function, or the image generation function described in each of the embodiments can be recorded on the computer-readable medium which is the tangible non-temporary information storage medium such as the optical disk, the magnetic disk, the semiconductor memory, or other objects, and the program can be provided through the information storage medium.

Further, instead of the aspect in which the program is stored in such a tangible non-temporary information storage medium and provided, the program signal can be provided as a download service by using a telecommunication line such as the Internet.

Further, a part or all of at least one processing function among the learning data generation function, the learning function, or the image generation function described in each of the embodiments are provided as an application server, and services that provide the processing function can be performed through the telecommunication line.

The computer that functions as the learning data generating unit 30 is understood as a learning data generating device. The computer that functions as the learning unit 40 is understood as a learning device.

About Hardware Configuration Of Each Processing Unit

The hardware structures of the processing units that execute various processing, such as the interpolation processing unit 12, the generator 14, and the addition unit 16 in FIG. 6, the image storage unit 24, the learning data generating unit 30, the learning unit 40, the GAN 41, the generator 42G, the discriminator 44D, the error calculating unit 50, and the optimizer 52 in FIG. 7, the fixed-size region cutout unit 31, the down-sampling processing unit 32, the up-sampling processing unit 34, the interpolation processing unit 35, and the Gaussian filter processing unit 36 in FIG. 8, and the high-frequency component extracting unit 33 in FIG. 21, are various processors as follows.

The various processors include the CPU that is a general-purpose processor executing the program and functioning as the various processing units, the GPU that is a processor specialized in the image processing, a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of these various processors or may be configured by two or more processors of the same type or different types. For example, one processing unit may be configured by a plurality of FPGAs, a combination of the CPU and the FPGA, or a combination of the CPU and the GPU. Alternatively, a plurality of processing units may be configured by one processor. As an example of configuring a plurality of processing units with one processor, first, as represented by a computer such as a client or a server, there is a form in which one processor is configured by a combination of one or more CPUs and the software and the processor functions as a plurality of processing units. Second, as represented by a system on chip (SoC), there is a form in which a processor is used in which the function of the entire system including a plurality of processing units is realized by a single integrated circuit (IC) chip. As described above, the various processing units are configured by one or more of the above various processors as a hardware structure.

Furthermore, the hardware structure of these various processors is, more specifically, an electric circuit (circuitry) in which the circuit elements such as semiconductor elements are combined.

Others

Here, the learning method of the super resolution generative model of the CT image has been described, but the learning method of the generative model according to the present disclosure is not applied only to the CT image, and can also be applied to various three-dimensional tomographic images. For example, the learning method may be applied to a magnetic resonance (MR) image acquired by a magnetic resonance imaging (MRI) device, a positron emission tomography (PET) image acquired by a PET device, an optical coherence tomography (OCT) image acquired by an OCT device, a three-dimensional ultrasound image acquired by a three-dimensional ultrasound imaging device, and the like.

Further, the learning method of the generative model according to the present disclosure is not applied only to the three-dimensional tomographic image, and can also be applied to various a two-dimensional image. For example, the learning method may be applied to an X-ray image. Further, the learning method is not applied only to the medical image, and can be applied to a normal camera image.

The technical scope of the present invention is not limited to the scope of the embodiments described above. The configurations and the like in the embodiments can be appropriately combined between the respective embodiments without departing from the spirit of the present invention.

EXPLANATION OF REFERENCES

10: super resolution image generating device
12: interpolation processing unit
14: generator
16: addition unit
20: learning system
24: image storage unit
30: learning data generating unit
31: fixed-size region cutout unit
32: down-sampling processing unit
33: high-frequency component extracting unit
34: up-sampling processing unit
35: interpolation processing unit
36: Gaussian filter processing unit
38: learning data storage unit
40: learning unit
41: generative adversarial network (GAN)
42G: generator
44D: discriminator
46: addition unit
50: error calculating unit
52: optimizer
70N: operation state
70P: operation state
500: computer
512: communicating unit
514: storage
516: operating unit
518: CPU
519: GPU
520: RAM
522: ROM
524: display unit
C01 to C05: convolutional layer
C1 to C10: convolutional layer
GT1: image
GT2: image
IM1 to IM4: CT image
IPT: interpolation image
LI1 to LI4: image
LK, LK1: thick slice image
LQ, LQ1: low resolution image
ORH, ORH1: real high resolution image
RH, RH1: real high resolution image
RHFC: real high-frequency component image
SAFM: self-attention feature map
SD: slice interval
ST: slice thickness
TCK: thick slice image
VH, VH1: virtual high resolution image
VHA1: image
VHN2: image
VHA3: image
VHA4: image
VHFC: high-frequency component image
VT: virtual thin slice image
S1 to S5: step of learning data generating processing
S11 to S19: step of learning processing

What is claimed is:

1. A learning method for performing machine learning of a generative model that estimates, from a first image, a second image including higher resolution image information than the first image, the method comprising:
   using a generative adversarial network including a generator which is the generative model and a discriminator which is an identification model that identifies whether provided data is data of a correct image for learning or data derived from an output from the generator;
   using, as learning data, a first learning image including first resolution information having a lower resolution than the second image and a second learning image including second resolution information having a higher resolution than the first learning image, the second learning image being the correct image corresponding to the first learning image;
   providing only the first learning image, among the first learning image and the second learning image, to be input to the generator; and
   implementing a self-attention mechanism only in a network of the discriminator among the generator and the discriminator, wherein the self-attention mechanism being applied in the network of the discriminator is a part or all of a plurality of convolutional layers of the discriminator.

2. The learning method according to claim 1,
wherein each network of the generator and the discriminator is a convolutional neural network.

3. The learning method according to claim 1,
wherein the first image is a three-dimensional tomographic image, and
the second image has at least a higher resolution than the first image in a slice thickness direction of the three-dimensional tomographic image.

4. The learning method according to claim 1,
wherein the second learning image is an image acquired by using a computed tomography device, and
the first learning image is an image generated by image processing based on the second learning image.

5. The learning method according to claim 4,
wherein the image processing of generating the first learning image from the second learning image includes down-sampling processing of the second learning image.

6. The learning method according to claim 5,
wherein the image processing of generating the first learning image from the second learning image includes up-sampling processing of an image obtained by the down-sampling processing by performing interpolation processing.

7. The learning method according to claim 4,
wherein the image processing of generating the first learning image from the second learning image includes smoothing processing using a Gaussian filter.

8. The learning method according to claim 1,
wherein the first learning images and the second learning images in a plurality of types of the learning data used for the machine learning have the same size, respectively.

9. The learning method according to claim 1,
wherein the second image is a high-frequency component image indicating information of a high-frequency component, and
the generator estimates a high-frequency component required to increase a resolution of an input image and outputs the high-frequency component image indicating the information of the high-frequency component.

10. The learning method according to claim 9, further comprising adding the high-frequency component image output from the generator and the image input to the generator,
wherein a virtual second image obtained by the adding is provided to be input to the discriminator.

11. A non-transitory computer-readable recording medium that causes a computer to execute the learning method according to claim 1 in a case in which a command stored in the recording medium is read by the computer.

12. A learned model that is learned by performing the learning method according to claim 1, the learned model being the generative model that estimates, from the first image, the second image including higher resolution image information than the first image.

13. A super resolution image generating device comprising the generative model which is a learned model that is learned by performing the learning method according to claim 1,
wherein the super resolution image generating device generates, from a third image which is input, a fourth image including higher resolution image information than the third image.

14. The super resolution image generating device according to claim 13,
wherein an image size of the third image is different from an image size of the first learning image.

15. The super resolution image generating device according to claim 13, further comprising:
a first interpolation processing unit that performs interpolation processing on the third image to generate an interpolation image; and
a first addition unit that adds the interpolation image and a high-frequency component generated by the generative model,
wherein the interpolation image is input to the generative model, and
the generative model generates the high-frequency component required to increase a resolution of the interpolation image.

16. A learning system for performing machine learning of a generative model that estimates, from a first image, a second image including higher resolution image information than the first image, the system comprising a generative adversarial network including a generator which is the generative model and a discriminator which is an identification model that identifies whether provided data is data of a correct image for learning or data derived from an output from the generator,
wherein a self-attention mechanism is implemented only in a network of the discriminator among the generator and the discriminator, wherein the self-attention mechanism being applied in the network of the discriminator is a part or all of a plurality of convolutional layers of the discriminator,
a first learning image including first resolution information having a lower resolution than the second image and a second learning image including second resolution information having a higher resolution than the first learning image, the second learning image being the correct image corresponding to the first learning image are used as learning data, and
only the first learning image among the first learning image and the second learning image is provided to be input to the generator and learning of the generative adversarial network is performed.

17. The learning system according to claim 16, further comprising a learning data generating unit that generates the learning data,
wherein the learning data generating unit includes
a fixed-size region cutout unit that cuts out a fixed-size region from an original image including the second resolution information, and
a down-sampling processing unit that performs down-sampling of an image of the fixed-size region cut out by the fixed-size region cutout unit,
the image of the fixed-size region cut out by the fixed-size region cutout unit is used as the second learning image, and
the first learning image is generated by performing down-sampling processing on the second learning image.

18. The learning system according to claim 17,
wherein the learning data generating unit further includes
a second interpolation processing unit that performs interpolation processing on an image obtained by the down-sampling processing, and
a smoothing processing unit that performs smoothing by using a Gaussian filter.

19. The learning system according to claim 16,
wherein the generator is configured to estimate a high-frequency component required to increase a resolution of an input image and output the high-frequency component image indicating the information of the high-frequency component, and the learning system further comprises a second addition unit that adds the high-frequency component image output from the generator and the image input to the generator.

\* \* \* \* \*